(12) United States Patent
Ganter et al.

(10) Patent No.: US 10,258,481 B2
(45) Date of Patent: Apr. 16, 2019

(54) MODULAR, CUSTOMIZABLE SPINE STABILIZATION SYSTEM

(71) Applicant: PARADIGM SPINE, LLC, New York, NY (US)

(72) Inventors: Detlev Ganter, Bräunlingen (DE); Stephan Eckhof, Rietheim-Weilheim (DE); Guntmar Eisen, Tuttlingen (DE); Sven Oliver Muckenfuß, Spaichingen (DE); Markus Salvermoser, Tuttlingen-Möhringen (DE)

(73) Assignee: PARADIGM SPINE, LLC, New York, NY (US)

( * ) Notice: Subject to any disclaimer, the term of this patent is extended or adjusted under 35 U.S.C. 154(b) by 0 days.

(21) Appl. No.: 15/877,236

(22) Filed: Jan. 22, 2018

(65) Prior Publication Data

US 2018/0153703 A1    Jun. 7, 2018

Related U.S. Application Data

(63) Continuation of application No. 14/216,638, filed on Mar. 17, 2014, now Pat. No. 9,872,777.
(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/442* (2013.01); *A61F 2/4455* (2013.01); *A61F 2/4611* (2013.01);
(Continued)

(58) Field of Classification Search
CPC .......... A61F 2/44; A61F 2/442; A61F 2/4425; A61F 2/4455; A61F 2/446; A61F 2/4465; A61F 2/447
(Continued)

(56) References Cited

U.S. PATENT DOCUMENTS

| 4,759,769 | A | * | 7/1988 | Hedman | ............... A61F 2/4425 623/17.13 |
| 5,370,697 | A | * | 12/1994 | Baumgartner | .......... A61F 2/442 623/17.15 |

(Continued)

FOREIGN PATENT DOCUMENTS

| FR | 2812806 A1 | 2/2002 |
| WO | 9965424 A2 | 12/1999 |

OTHER PUBLICATIONS

Extended European Search Report for EP Appl. No. 14765710 dated Jan. 2, 2017.
(Continued)

*Primary Examiner* — Eric S Gibson
(74) *Attorney, Agent, or Firm* — Farber LLC; Tram Anh Nguyen

(57) ABSTRACT

A modular, customizable system that provides components for assembling an implantable device is provided. The system allows the user to assemble an implantable spine stabilization device that is flexible and allows dynamic stabilization. The same system also provides components for assembling a rigid or non-flexible fusion-enabling spine stabilization device. The components of the system are easily interchangeable, allowing the user the ability to customize the assembled device for a true fit with the patient, as well as allow an easy conversion of the dynamic device into a fusion-enabling device. Associated insertion instruments and methods of use are also disclosed.

19 Claims, 31 Drawing Sheets

US 10,258,481 B2
Page 2

Related U.S. Application Data

(60) Provisional application No. 61/792,173, filed on Mar. 15, 2013.

(52) U.S. Cl.
CPC ...... *A61F 2/4684* (2013.01); *A61F 2002/305* (2013.01); *A61F 2002/30018* (2013.01); *A61F 2002/3093* (2013.01); *A61F 2002/30131* (2013.01); *A61F 2002/30247* (2013.01); *A61F 2002/30387* (2013.01); *A61F 2002/30433* (2013.01); *A61F 2002/30471* (2013.01); *A61F 2002/30538* (2013.01); *A61F 2002/30563* (2013.01); *A61F 2002/30578* (2013.01); *A61F 2002/30604* (2013.01); *A61F 2002/30733* (2013.01); *A61F 2002/30787* (2013.01); *A61F 2002/30904* (2013.01)

(58) Field of Classification Search
USPC .......................................... 623/17.11–17.16
See application file for complete search history.

(56) References Cited

U.S. PATENT DOCUMENTS

| | | | |
|---|---|---|---|
| 5,645,599 A * | 7/1997 | Samani | A61B 17/7062 606/248 |
| 5,676,702 A * | 10/1997 | Ratron | A61F 2/442 623/17.16 |
| 5,989,291 A * | 11/1999 | Ralph | A61F 2/442 623/17.15 |
| 6,059,829 A * | 5/2000 | Schlapfer | A61F 2/4455 606/247 |
| 6,063,121 A * | 5/2000 | Xavier | A61F 2/4425 606/247 |
| 6,102,950 A * | 8/2000 | Vaccaro | A61F 2/4611 606/247 |
| 6,156,067 A * | 12/2000 | Bryan | A61B 17/686 606/247 |
| 6,228,118 B1 * | 5/2001 | Gordon | A61F 2/4425 623/17.14 |
| 6,656,224 B2 * | 12/2003 | Middleton | A61F 2/30744 623/17.16 |
| 6,733,532 B1 * | 5/2004 | Gauchet | A61F 2/442 606/247 |
| 6,863,689 B2 * | 3/2005 | Ralph | A61B 17/025 623/17.11 |
| 6,969,405 B2 * | 11/2005 | Suddaby | A61F 2/441 623/17.12 |
| 7,014,658 B2 * | 3/2006 | Ralph | A61F 2/442 623/17.13 |
| 7,025,787 B2 * | 4/2006 | Bryan | A61B 17/1671 623/17.15 |
| 7,056,344 B2 * | 6/2006 | Huppert | A61F 2/4425 623/17.11 |
| 7,169,182 B2 * | 1/2007 | Errico | A61F 2/442 606/914 |
| 7,195,644 B2 * | 3/2007 | Diaz | A61F 2/4425 623/17.13 |
| 7,214,244 B2 * | 5/2007 | Zubok | A61F 2/4425 623/17.13 |
| 7,393,361 B2 * | 7/2008 | Zubok | A61F 2/4425 623/17.15 |
| 7,468,076 B2 * | 12/2008 | Zubok | A61F 2/4425 623/16.11 |
| 7,491,239 B2 * | 2/2009 | Doubler | A61F 2/4425 623/17.14 |
| 7,491,241 B2 * | 2/2009 | Errico | A61F 2/4425 606/86 A |
| 7,550,008 B2 * | 6/2009 | Ralph | A61B 17/025 623/17.11 |
| 7,578,849 B2 * | 8/2009 | Trieu | A61F 2/442 606/248 |
| 7,682,376 B2 * | 3/2010 | Trieu | A61B 17/7062 606/248 |
| 7,691,130 B2 * | 4/2010 | Bruneau | A61B 17/7062 606/249 |
| 7,740,658 B2 * | 6/2010 | Eckman | A61F 2/4611 623/17.11 |
| 7,815,663 B2 * | 10/2010 | Trieu | A61B 17/7026 606/254 |
| 7,879,101 B2 * | 2/2011 | Petit | A61F 2/4425 623/17.15 |
| 7,959,678 B2 * | 6/2011 | Filippi | A61F 2/4425 623/17.14 |
| 8,029,569 B2 * | 10/2011 | Aferzon | A61F 2/4425 623/17.12 |
| 8,152,850 B2 * | 4/2012 | Copf, Jr. | A61F 2/4425 623/17.15 |
| 8,262,735 B2 * | 9/2012 | Aferzon | A61F 2/4425 623/17.12 |
| 8,425,609 B2 * | 4/2013 | Zubok | A61F 2/4425 623/17.16 |
| 8,545,564 B2 * | 10/2013 | Errico | A61B 17/025 623/17.14 |
| 8,585,764 B2 * | 11/2013 | Copf, Jr. | A61F 2/4425 623/17.11 |
| 8,808,384 B2 * | 8/2014 | Arramon | A61F 2/4425 623/17.11 |
| 8,968,365 B2 * | 3/2015 | Aschmann | A61B 17/7062 606/248 |
| 8,968,407 B2 * | 3/2015 | Filippi | A61F 2/4425 623/17.16 |
| 9,044,336 B2 * | 6/2015 | Aferzon | A61F 2/4425 |
| 9,084,688 B2 * | 7/2015 | Hes | A61F 2/4425 |
| 9,149,366 B2 * | 10/2015 | Prevost | A61F 2/4455 |
| 9,265,618 B2 * | 2/2016 | Rashbaum | A61F 2/4425 |
| 9,289,310 B2 * | 3/2016 | Chaput | A61B 17/686 |
| 9,289,311 B1 * | 3/2016 | Whipple | A61F 2/4425 |
| 9,414,932 B2 * | 8/2016 | Errico | A61F 2/442 |
| 9,872,777 B2 * | 1/2018 | Ganter | A61F 2/442 |
| 2002/0128715 A1 * | 9/2002 | Bryan | A61B 17/02 623/17.15 |
| 2003/0040802 A1 * | 2/2003 | Errico | A61F 2/442 623/17.14 |
| 2003/0069586 A1 * | 4/2003 | Errico | A61F 2/442 606/99 |
| 2003/0069642 A1 * | 4/2003 | Ralph | A61F 2/4425 623/17.13 |
| 2003/0069643 A1 * | 4/2003 | Ralph | A61F 2/4425 623/17.13 |
| 2003/0135277 A1 * | 7/2003 | Bryan | A61B 17/1671 623/17.12 |
| 2003/0135278 A1 * | 7/2003 | Eckman | A61F 2/4425 623/17.14 |
| 2003/0216810 A1 * | 11/2003 | Ralph | A61F 2/4425 623/17.14 |
| 2003/0220691 A1 * | 11/2003 | Songer | A61F 2/442 623/17.14 |
| 2004/0006343 A1 * | 1/2004 | Sevrain | A61B 17/7059 606/279 |
| 2004/0034422 A1 * | 2/2004 | Errico | A61F 2/442 623/17.11 |
| 2004/0034426 A1 * | 2/2004 | Errico | A61F 2/442 623/17.13 |
| 2004/0054411 A1 * | 3/2004 | Kelly | A61B 17/02 623/17.13 |
| 2004/0093082 A1 * | 5/2004 | Ferree | A61F 2/4425 623/17.11 |
| 2004/0127994 A1 * | 7/2004 | Kast | A61F 2/447 623/17.16 |
| 2004/0158325 A1 * | 8/2004 | Errico | A61B 17/025 623/17.11 |
| 2004/0220671 A1 * | 11/2004 | Ralph | A61F 2/4425 623/17.15 |
| 2004/0225295 A1 * | 11/2004 | Zubok | A61F 2/442 606/90 |
| 2005/0043804 A1 * | 2/2005 | Gordon | A61F 2/442 623/17.16 |

(56) References Cited

U.S. PATENT DOCUMENTS

| | | | |
|---|---|---|---|
| 2005/0065611 A1* | 3/2005 | Huppert | A61F 2/4425 623/17.15 |
| 2005/0125063 A1* | 6/2005 | Matge | A61F 2/442 623/17.13 |
| 2005/0165486 A1* | 7/2005 | Trieu | A61F 2/442 623/17.13 |
| 2005/0187631 A1* | 8/2005 | Van Hoeck | A61F 2/442 623/17.13 |
| 2005/0187632 A1* | 8/2005 | Zubok | A61F 2/4425 623/17.14 |
| 2005/0192670 A1* | 9/2005 | Zubok | A61F 2/4425 623/17.13 |
| 2005/0228500 A1* | 10/2005 | Kim | A61F 2/4425 623/17.13 |
| 2005/0234553 A1* | 10/2005 | Gordon | A61F 2/442 623/17.13 |
| 2005/0246022 A1* | 11/2005 | Zubok | A61F 2/4425 623/17.11 |
| 2005/0261772 A1* | 11/2005 | Filippi | A61F 2/4425 623/17.13 |
| 2006/0036327 A1* | 2/2006 | Enayati | A61F 2/4425 623/17.15 |
| 2006/0089714 A1* | 4/2006 | Liu | A61F 2/4425 623/17.11 |
| 2006/0129240 A1* | 6/2006 | Lessar | A61F 2/4425 623/17.14 |
| 2006/0142862 A1* | 6/2006 | Diaz | A61F 2/4425 623/17.13 |
| 2006/0190084 A1* | 8/2006 | Doubler | A61F 2/4425 623/17.14 |
| 2006/0235524 A1* | 10/2006 | Petit | A61F 2/4425 623/17.13 |
| 2006/0235525 A1* | 10/2006 | Gil | A61F 2/4425 623/17.13 |
| 2006/0241766 A1* | 10/2006 | Felton | A61F 2/4425 623/17.12 |
| 2006/0247770 A1 | 11/2006 | Peterman | |
| 2006/0247773 A1* | 11/2006 | Stamp | A61B 5/076 623/17.11 |
| 2006/0247777 A1* | 11/2006 | Stamp | A61F 2/4425 623/17.14 |
| 2006/0265068 A1* | 11/2006 | Schwab | A61B 17/7067 623/17.11 |
| 2006/0293752 A1* | 12/2006 | Moumene | A61F 2/4425 623/17.13 |
| 2007/0162130 A1* | 7/2007 | Rashbaum | A61F 2/4425 623/17.11 |
| 2007/0191953 A1* | 8/2007 | Trieu | A61F 2/442 623/17.15 |
| 2007/0198092 A1* | 8/2007 | Errico | A61F 2/4611 623/17.14 |
| 2007/0225806 A1* | 9/2007 | Squires | A61F 2/442 623/17.11 |
| 2007/0233255 A1* | 10/2007 | Song | A61F 2/4425 623/17.11 |
| 2007/0233261 A1* | 10/2007 | Lopez | A61F 2/4425 623/17.13 |
| 2008/0015704 A1* | 1/2008 | Gradl | A61F 2/44 623/17.16 |
| 2008/0114453 A1* | 5/2008 | Francis | A61F 2/4425 623/17.14 |
| 2008/0183295 A1* | 7/2008 | Aferzon | A61F 2/442 623/17.16 |
| 2008/0221690 A1* | 9/2008 | Chaput | A61B 17/686 623/17.16 |
| 2008/0221691 A1* | 9/2008 | Chaput | A61B 17/686 623/17.16 |
| 2009/0076608 A1* | 3/2009 | Gordon | A61F 2/4425 623/17.16 |
| 2009/0125111 A1* | 5/2009 | Copf, Jr. | A61F 2/4425 623/17.16 |
| 2009/0143861 A1* | 6/2009 | Errico | A61B 17/025 623/17.16 |
| 2010/0234956 A1* | 9/2010 | Attia | A61F 2/447 623/17.16 |
| 2010/0286777 A1* | 11/2010 | Errico | A61F 2/442 623/17.11 |
| 2010/0298941 A1* | 11/2010 | Hes | A61F 2/4425 623/17.16 |
| 2011/0022177 A1* | 1/2011 | Yeh | A61F 2/442 623/17.15 |
| 2011/0046744 A1* | 2/2011 | Errico | A61B 17/025 623/17.16 |
| 2011/0238185 A1* | 9/2011 | Filippi | A61F 2/4425 623/17.16 |
| 2011/0282458 A1* | 11/2011 | Aferzon | A61F 2/442 623/17.16 |
| 2011/0301612 A1* | 12/2011 | Richter | A61F 2/4425 606/99 |
| 2012/0150298 A1* | 6/2012 | Bennett | A61F 2/4425 623/17.11 |
| 2012/0165948 A1* | 6/2012 | Copf, Jr. | A61F 2/4425 623/17.16 |
| 2012/0239148 A1* | 9/2012 | Aferzon | A61F 2/442 623/17.15 |
| 2013/0274880 A1* | 10/2013 | Arramon | A61F 2/4425 623/17.15 |
| 2013/0317615 A1* | 11/2013 | Jimenez | F16C 11/12 623/17.15 |
| 2014/0309741 A1* | 10/2014 | Ganter | A61F 2/442 623/17.16 |
| 2014/0336769 A1* | 11/2014 | Errico | A61B 17/025 623/17.16 |
| 2015/0257897 A1* | 9/2015 | Aferzon | A61F 2/442 623/17.15 |
| 2015/0272743 A1* | 10/2015 | Jimenez | A61F 2/447 623/17.16 |
| 2015/0282952 A1* | 10/2015 | Hes | A61F 2/4425 623/17.15 |
| 2015/0374508 A1* | 12/2015 | Sandul | A61F 2/447 623/17.16 |
| 2016/0022438 A1* | 1/2016 | Lamborne | A61F 2/4455 623/17.16 |
| 2016/0038305 A1* | 2/2016 | Weiman | A61F 2/4455 623/17.16 |
| 2016/0089247 A1* | 3/2016 | Nichols | A61F 2/30767 623/17.16 |

OTHER PUBLICATIONS

International Search Report and Written Opinion for PCT/US2014/030585 dated Aug. 22, 2014.

* cited by examiner

MODULAR, CUSTOMIZABLE SPINE STABILIZATION SYSTEM

CROSS-REFERENCE TO RELATED APPLICATIONS

This application is a continuation application of U.S. patent application Ser. No. 14/216,638 filed Mar. 17, 2014 (allowed), which claims priority to U.S. Provisional No. 61/792,173 filed Mar. 15, 2013 and entitled "MODULAR, CUSTOMIZABLE SPINE STABILIZATION SYSTEM," the contents of which are incorporated in their entirety by reference.

FIELD

The present disclosure relates to implantable spine stabilization devices, associated insertion instruments and related methods. More specifically, the present disclosure relates to a modular, customizable system that provides components for assembling an implantable spine stabilization device that can be flexible and allow dynamic stabilization in one application, and converted into a rigid or non-flexible fusion-enabling device in another application.

BACKGROUND

Fusion of the spine is a well-known and widely practiced medical procedure to alleviate severe back and/or neck pain due to misaligned, damaged or otherwise diseased spines. In some cases, the fusion is carried out by implanting a cage, or implantable device having an opening for the ingrowth of tissue therethrough, at the level of the spine to be fused. The opening may be filled with, or contain, bone graft material, bone chips or other biologically active material that enhances fusion.

Where it is difficult to maneuver and insert a rigid implantable device due to the size limitations or delicate anatomical site (i.e., closeness to nerves or spinal cord, e.g.) of the area to be implanted, it is desirable to provide an implant that may be converted from a flexible implant into a rigid one that can promote fusion. Expandable fusion cages are well known in the art. Most of these fusion cages comprise two or more components that cooperate together to form a fusion promoting device. For instance, a typical expandable spinal implant can comprise a flexible fusion cage and a corresponding insert that, when inserted, expands the fusion cage.

As further examples of expandable spinal implants, U.S. Patent Application Publication No. 2010/0234956 entitled "EXPANDING CAGE FOR VERTEBRAL SURGERY" to Attia et al. describes an expanding intervertebral implant comprising an intervertebral fusion cage and an insertable rod for placement inside the cage to expand the cage after implantation. U.S. Pat. No. 7,578,849 entitled "INTERVERTEBRAL IMPLANTS AND METHODS OF USE" by Trieu described another two-component intervertebral spinal stabilization implant having a fusion cage and an elastic component for insertion into the fusion cage. U.S. Pat. No. 6,102,950 entitled "INTERVERTEBRAL BODY FUSION DEVICE" by Vaccaro describes a two-component fusion promoting implant comprising an intervertebral body fusion device having a cage component for placement intervertebrally, and a wedge body that is insertable into the cage component.

However, these expandable spinal implants are not intended for use without their inserts. In other words, these implants are not configured for conversion from a functional dynamic implant into a fusion implant at a later time.

Dynamic implants having the desired anatomical shape and size conducive for dynamic spinal stabilization are known. One such implant is described in U.S. Pat. No. 7,867,276 entitled "DYNAMIC INTERVERTEBRAL IMPLANT" by Matge. However, this dynamic intervertebral implant is not configured to be easily converted into a fusion promoting implant at a later time.

Accordingly, there exists a need for a modular, convertible implant system that can be used in either dynamic or fusion-promoting modes, or both, at different points of time.

SUMMARY

The present disclosure provides a modular, customizable system that provides components for assembling an implantable spine stabilization device that can be flexible and allow dynamic stabilization in one application, and converted into a rigid or non-flexible fusion-enabling device in another application. The assembled devices may be configured for use in the lumbar, thoracic, or cervical region of the spine. Methods for implantation and use are also disclosed, along with associated insertion instruments and tools.

In one exemplary embodiment, an implantable spine stabilization device is provided. The device may comprise a main body having a superior plate, inferior plate, and a flexible sidewall connecting the superior and inferior plates, the superior plate having an opening extending therethrough for receiving a domed cap, the domed cap comprising a domed top and a stem configured for insertion into the opening on the superior plate, wherein the main body is compressible and distractable.

In one embodiment, the domed cap may be eccentric. In another embodiment, the cap may centric. In still another embodiment, the inferior plate may also include an opening for receiving a domed cap. The device is configured to be implantable in both a lateral and a ventral approach.

In another exemplary embodiment, an implantable spine stabilization device is provided. The device may comprise a compressible and distractable main body having a superior plate, inferior plate, and a flexible sidewall connecting the superior and inferior plates, the superior plate having an opening extending therethrough for receiving a domed cap, the domed cap comprising a domed top and a stem configured for insertion into the opening on the superior plate, the domed top including a through-hole. A compression-blocking insert configured for placement in between the superior and inferior plates may also be provided, the insert being sized to fit entirely within the main body.

In one embodiment, the through-hole of the domed top may be filled with bone graft material, bone cement, bone substitute material, bone hardening material, bone void filler, demineralized bone matrix, or other similar materials. The domed cap may be eccentric, or it may be centric, and may also include surface features or a coating to enhance bone growth. In still another embodiment, the inferior plate may also include an opening for receiving a domed cap. The device is configured to be implantable in both a lateral and a ventral approach.

In still another exemplary embodiment, a modular spine stabilization system is provided. The system may comprise a plurality of compressible and distractable main bodies, each main body having a superior plate, inferior plate, and a flexible sidewall connecting the superior and inferior plates. The system may further include a plurality of domed caps, each domed cap comprising a domed top and a stem configured for insertion into an opening on the superior plate. A plurality of compression-blocking inserts can also be provided with the system. Each of the inserts may be configured for placement in between the superior and inferior plates, the insert being sized to fit entirely within the main body.

In yet another embodiment, the domed top may include a through-hole that can also be filled with bone graft material, bone cement, bone substitute material, bone hardening material, bone void filler, or other similar materials. The domed cap may be eccentric, or it may be centric, and may also include surface features or a coating to enhance bone growth. In still another embodiment, the inferior plate may also include an opening for receiving a domed cap. This domed cap for the inferior plate may optionally include a through-hole that can also be filled with bone graft material, bone cement, bone substitute material, bone hardening material, bone void filler, demineralized bone matrix, or other similar materials.

In yet another exemplary embodiment, a method of treating a spinal instability of an intervertebral space is provided. The method may comprise the steps of: providing a modular spine stabilization system comprising: a plurality of compressible and distractable main bodies, each main body having a superior plate, inferior plate, and a flexible sidewall connecting the superior and inferior plates; a plurality domed caps, each domed cap comprising a domed top and a stem configured for insertion into an opening on the superior plate; and a plurality of compression-blocking inserts, each insert being configured for placement in between the superior and inferior plates, the insert being sized to fit entirely within the main body; selecting a main body for insertion into the intervertebral space; selecting a domed cap based on a morphological profile of the intervertebral space; attaching the domed cap to the superior plate of the main body; compressing the main body; and inserting the main body into the intervertebral space.

A trial may be used prior to implantation to ascertain the morphology of the intervertebral space, and to determine the appropriate sized and/or shaped domed cap to insert into the main body. The step of inserting the compression-blocking insert may also comprise selecting an insert having a height that adjusts lordotic curvature, such as a height greater than the device. The insert may also be angled and thus provide distraction as well as lodortic adjustment to achieve sagittal balance. Additionally, a compression-blocking insert may be selected having an appropriate angle such that, when inserted, will adjust the angle of the device itself.

The implantable devices of the present disclosure may be suitable for either dynamic spine stabilization, or for fusion applications, or both. For example, it is possible to convert a previously dynamic spine stabilization device into a fusion-enabling device by the introduction of the compression-blocking inserts of the present disclosure. In some cases, it is also possible to implant the device with the insert in a fusion-promoting situation, and then remove the insert at a later time to allow dynamic stabilization with the device.

The devices are configured to be stand-alone devices. However, it is also possible to utilize these devices with a posterior fixation device or system for total 360 degree stabilization. In some embodiments, the devices may be configured for use with fixation screws. For instance, in one exemplary embodiment, the compression-blocking insert may be configured for attachment to the vertebral bodies with fixation screws. In one embodiment, the inserts may comprise an attachment plate for receiving the fixation screws. In another embodiment, the fixation screws may be attached to the main body.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 3A-3G illustrate an exemplary embodiment of a spine stabilization device of the present disclosure, in which:

FIG. 3A shows an exploded view of the spine stabilization device;

FIG. 3B shows a top planar view of the spine stabilization device of FIG. 3A;

FIGS. 3C and 3D illustrate alternative ways to attach the body of the spine stabilization device with the domed cap;

FIG. 3E shows a cutaway view of the domed cap attached to the body of the spine stabilization device;

FIG. 3F shows a side view of the spine stabilization device of FIG. 3E; and

FIG. 3G shows a bottom perspective view of the spine stabilization device of FIG. 3E.

FIGS. 4A-4D illustrate an exemplary embodiment of another spine stabilization device, in which:

FIG. 4A shows an exploded view of the spine stabilization device;

FIG. 4B illustrates a partial cutaway view of the spine stabilization device of FIG. 4A;

FIG. 4C illustrates a side view of the spine stabilization device of FIG. 4A; and FIG. 4D illustrates a front view of the spine stabilization device of FIG. 4A.

FIGS. 11A-11F illustrate another exemplary embodiment of a spine stabilization device of the present disclosure having a fusion-enabling insert configured for external fixation, in which:

FIGS. 11A-11C show the spine stabilization device secured to the side of the vertebral bodies, wherein FIG. 11A shows a side perspective view, FIG. 11B shows a front perspective view, and FIG. 11C shows an enlarged cutaway view in situ; and FIGS. 11D-11F show the spine stabilization device secured to the front of the vertebral bodies, wherein FIG. 11D shows a side perspective view, FIG. 11E shows a front perspective view, and FIG. 11F shows an enlarged cutaway view in situ.

FIGS. 12A-12D illustrate still another exemplary embodiment of a spine stabilization device of the present disclosure having a fusion-enabling insert configured for external fixation, in which:

FIGS. 12A and 12B show the spine stabilization device secured to the side of the vertebral bodies, wherein FIG. 12A shows a side perspective view and FIG. 12B shows a front perspective view in situ; and FIGS. 12C and 12D show the spine stabilization device secured to the front of the vertebral bodies, wherein FIG. 12C shows a front perspective view and FIG. 12D shows a side perspective view in situ.

FIGS. 13A and 13B illustrate yet another exemplary embodiment of a spine stabilization device of the present disclosure configured for external fixation, wherein FIG. 13A shows a front perspective view and FIG. 13B shows a side perspective view in situ.

The foregoing and other features of the present disclosure will become apparent to one skilled in the art to which the present disclosure relates upon consideration of the following description of exemplary embodiments with reference to the accompanying drawings.

DETAILED DESCRIPTION OF THE EMBODIMENTS

A modular, customizable system that provides components for assembling an implantable device is provided. The system allows the user to assemble an implantable spine stabilization device that is flexible and allows dynamic stabilization. The same system also provides components for assembling a rigid or non-flexible fusion-enabling spine stabilization device. The components of the system are easily interchangeable, allowing the user the ability to customize the assembled device for a true fit with the patient, as well as allow an easy conversion of the dynamic device into a fusion-enabling device, if so desired. For instance, implantable spine stabilization devices that can be compressed for ease of insertion, and structurally strong enough to dynamically stabilize the spine are desirable. The present system provides a compressible spine stabilization device that is easy to insert and use to dynamically stabilize the region of the spine for some duration of time. Then, when it is desired or necessary to fuse the same region, that dynamic device may be easily converted into a rigid or non-flexible fusion-enabling device. In other cases, the user may simply elect to assemble a dynamic or a fusion device initially, and select those components from the system to achieve that goal. The devices may be configured for use in the lumbar, thoracic, or cervical region of the spine. Methods for implantation and use are also disclosed, along with associated insertion instruments and tools.

Figure 1:
FIG. 1 illustrates an exemplary spine and an intervertebral space to be stabilized using the device of the present disclosure.

FIG. 1 illustrates an exemplary spine and an intervertebral space that can receive the spine stabilization device of the present disclosure. As shown, the space may be located in the lumbar region of the spine. However, it is understood that the spine stabilization device of the present disclosure may be sized and configured for insertion in the thoracic or cervical region, if so desired.

Figure 2:
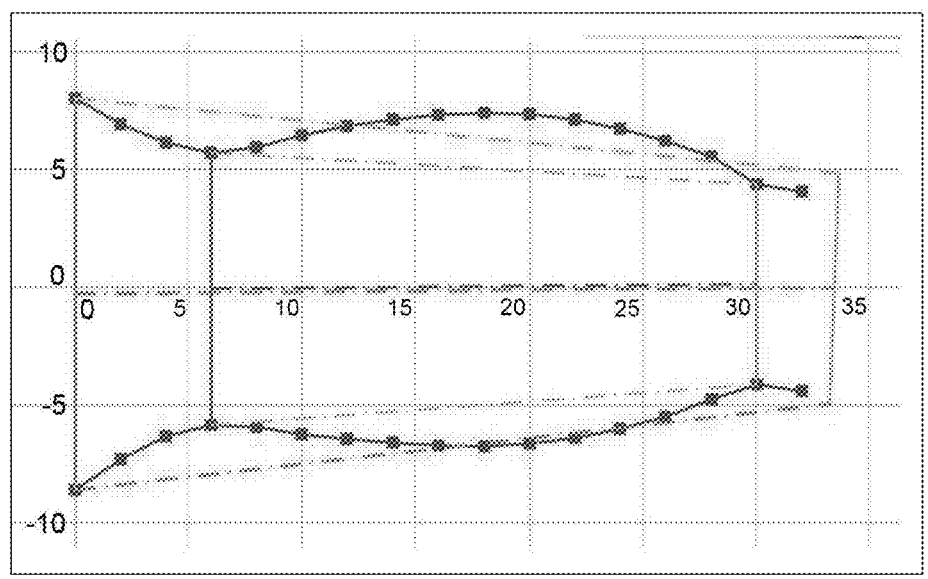
FIG. 2 illustrates a graphical representation of the morphological profile of the intervertebral space of FIG. 1.

The spine stabilization devices provided herein are configured to be inserted between the vertebrae of a spine. The devices may be used either with or without additional fixation elements, such as for example, screws, nuts, bolts, fasteners, glue, etc. In order to be able to stabilize the intervertebral space, the devices are customizable and configured to closely match the morphology of the intervertebral space. In developing the interchangeable components of the device, certain physical parameters that were evaluated included: A-P diameter, wedge angle, disc height, apex height, apex diameter, and apex position, etc. These parameters provided a basis to model the morphological profile of the physical implantation site, particularly the endplate morphology, and thus to also model the overall geometry of the spine stabilization devices of the present disclosure. FIG. 2 shows an exemplary morphological profile created using the data listed above.

Accordingly, the present disclosure provides spine stabilization devices that are customizable and configured to closely match the morphology of the implantation site, particularly the endplates, such that the devices can be securely positioned in the intervertebral space, either with or without the use fixation elements. The system of the present disclosure provides the user with the ability to assemble anterior stand-alone devices that can act as either a dynamic cage or a fusion cage.

The system provides interchangeable components to create spine stabilization devices with any number of footprint sizes, with any number of lodortic angles and heights, to provide a combination of geometries that are morphologically suitable for the implantation site. For example, in one exemplary embodiment the spine stabilization device may have a footprint size of about 30 mm by about 39 mm. In another exemplary embodiment, the footprint size may be about 27 mm by about 35 mm. Generally speaking, the footprint may be in the range of about 20 mm by about 50 mm, depending on the region of the spine to be treated, and the size of the patient. Likewise, the system may provide devices with various lodortic angles, including but not limited to 0 degrees, 3 degrees, and 7 degrees. Of course, it is understood that other angles may also be provided, and fractions thereof, such as for example, 2.75 degrees or 8.24 degrees. Generally speaking, the lodortic angle may be in the range of 0 to about 12 degrees. Additionally, the devices may be provided with any number of different heights. Some exemplary heights may include: about 8, about 10, and about 12 mm. Generally speaking, the devices may have heights ranging from about 3 mm to about 18 mm. It is understood, of course, that the dimensions provided herein are merely exemplary and not to be limiting. These specific examples are intended to show the many different ways the devices may be assembled to provide numerous configurations for the final geometry of the device.

As mentioned, the system provides spine stabilization devices that are able to be compressed for easy insertion. To assemble, or later convert the spine stabilization devices to, fusion-enabling implants, the devices may be easily blocked using an insert such that no compression is possible. Additionally, these devices may be able to distract for sagittal adjustment in the case of fusion. The system provides these blocking inserts in a variety of heights, thereby allowing the user to effectively customize the height of the implantable device by the use of differently sized blocking inserts. In other words, putting in different sized inserts alters the curvature of the device as well as alters the angle between different implant sizes. For example, it is possible to go from 5 degrees to 7 degrees with the use of a larger blocking insert. Accordingly by this manner, the spine stabilization devices of the present disclosure are considered to provide standalone devices that allow 360 degrees of stabilization, i.e., without the need for a posterior stabilization component.

Figure 3A:
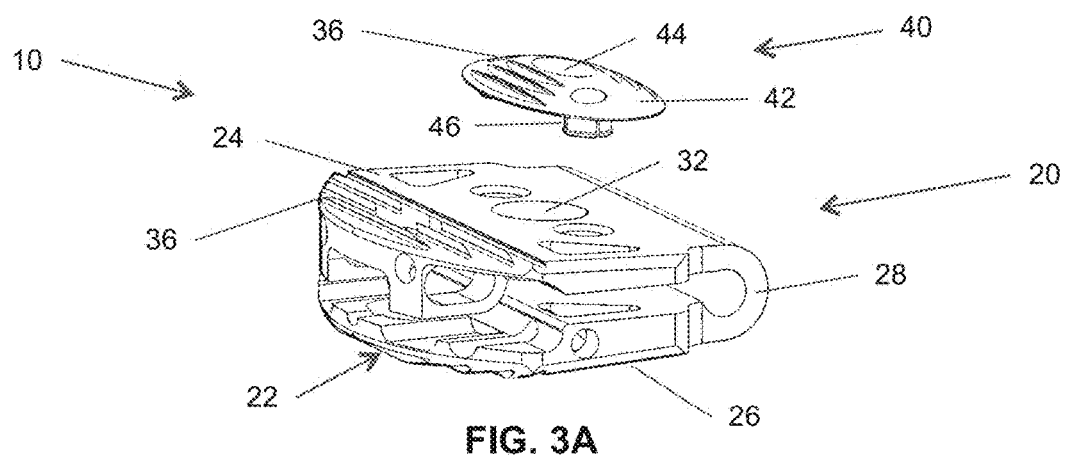

Turning now to the drawings and particularly to FIGS. 3A-3G, an exemplary embodiment of a modular, customizable system 10 is shown. The system allows a dynamic spine stabilization device 20 to be assembled. This device may comprise a main body 22 having a superior plate 24 and inferior plate 26 connected by a sidewall 28 for compressibility. The superior plate 24 may include an opening 32 for receiving a domed cap 40, as shown in FIG. 3A. The domed cap 40 may comprise a domed upper surface 42, a through-hole 44, and a stem 46 that is configured to lock into the opening 32 on the superior plate 24. The domed upper surface 42 may comprise ridges, cutout portions, teeth, or other surface features 36. These surface features may also be provided on the superior and inferior plates of the main body as well.

Figure 3B:
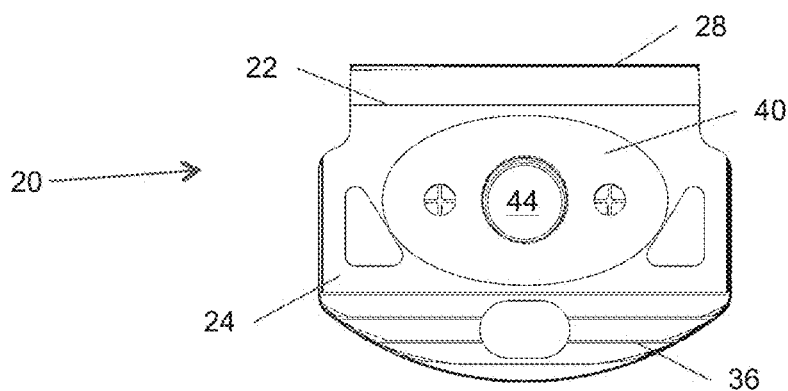
Figure 3D:
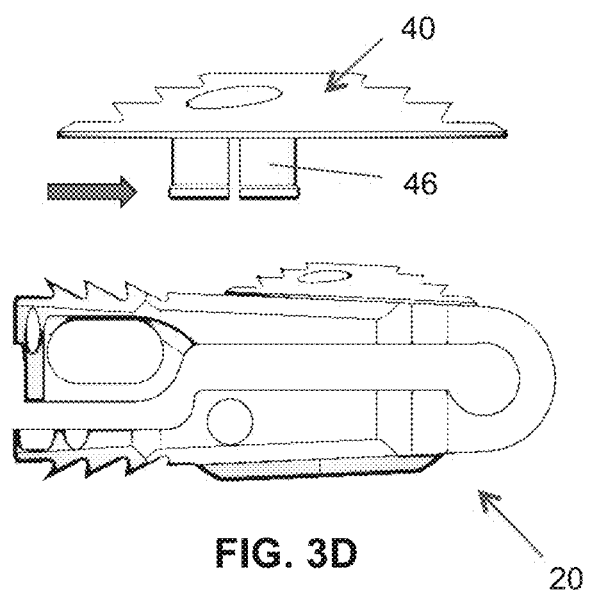
Figure 3C:
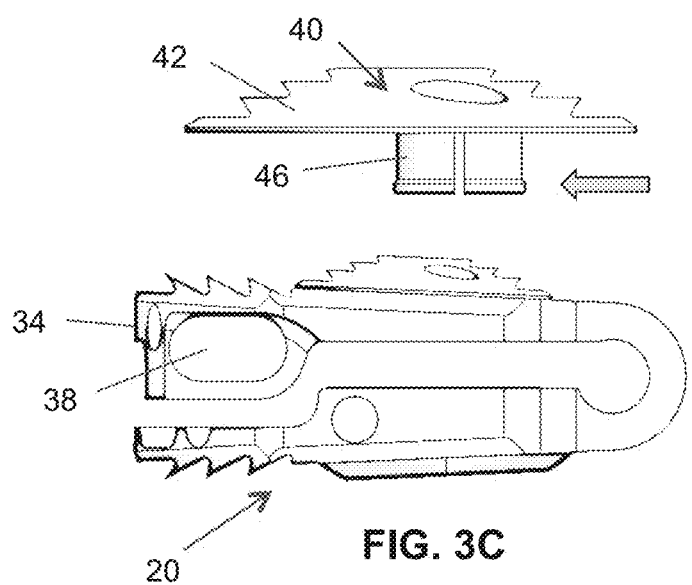

FIG. 3B shows a top planar view of the spine stabilization device of FIG. 3A. As shown in FIGS. 3C and 3D, the domed cap 40 is not symmetrical, and thus can be snapped onto the main body 22 in different directions. This eccentric domed cap allows for variations the direction of the cap, and hence the curvature of the superior plate. For example, as shown in FIGS. 3C and 3D, the domed cap may be positioned in inapposite directions relative to the main body 22 of the spine stabilization device. This gives the user the ability to adjust the curvature of the device to closely match the patient's anatomy. In other words, the user may adapt morphologically by adjusting the position of the domed cap. As shown, the domed cap 40 may be eccentric. However, in other embodiments the domed cap 40 may be centric.

Figure 3E:
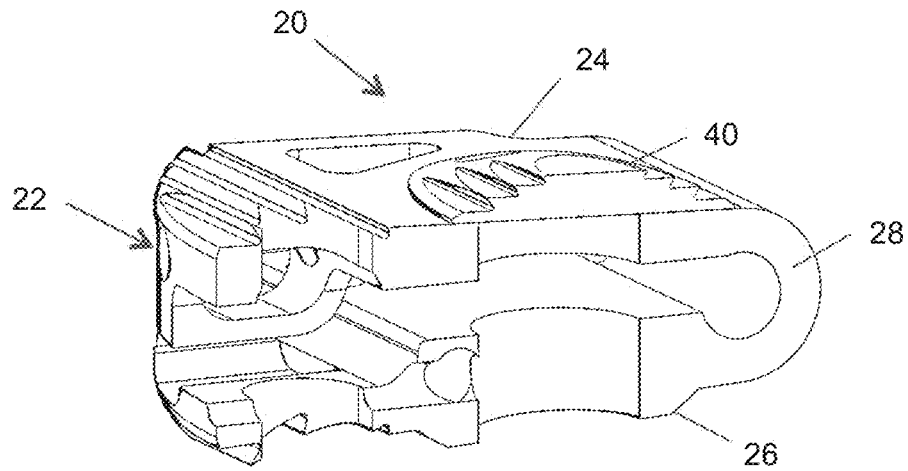

FIG. 3E shows a cutaway view of the domed cap 40 attached to the body of the spine stabilization device 20, which shows the close fit between the cap and the superior plate of the main body. It is intended that the domed cap 40 be configured to easily snap onto the superior plate 24 such that the surgeon may be able to perform this task very quick prior to implantation. The domed cap 40 may comprise a stem 46 which comprises a plurality of movable fingers, thus allowing the stem to be snapped onto the superior plate. However, other mechanisms for attaching the domed cap to the plate may be utilized, such as by threads, dovetail connection, press-fit, etc.

Figure 3F:
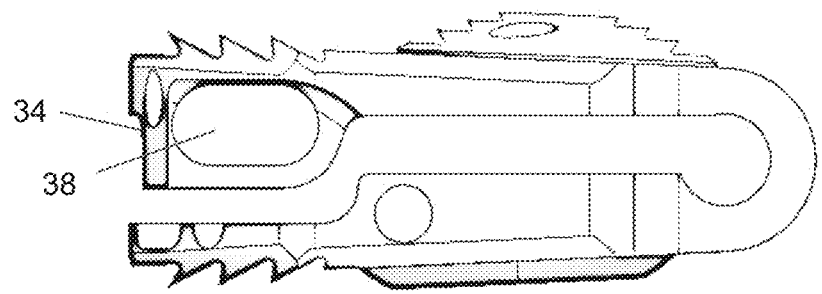

FIG. 3F shows a side view of the spine stabilization device of FIG. 3E. As can be seen, within the main body, tool-engaging openings 38 are provided on the superior plate 24 to allow the user a way to manipulate the main body and control the manner of compression. These tool-engaging openings may be provided on an undermounted bracket or panel 34 that extends from the underside of the superior plate 24.

Figure 3G:
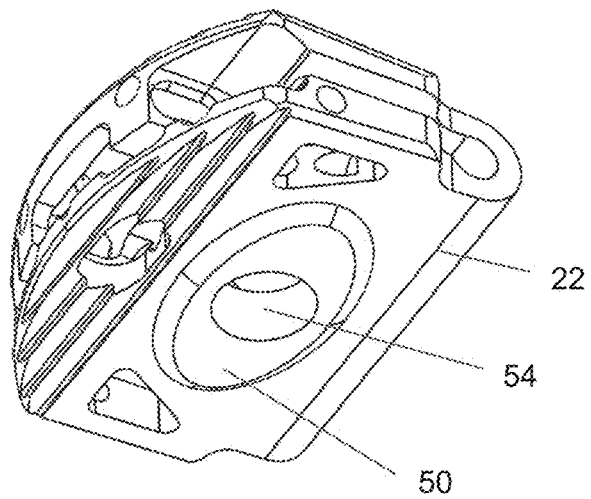

FIG. 3G shows a bottom perspective view of the spine stabilization device of FIG. 3E. The inferior plate 26 may also include an opening within which resides a bottom cap 50. This bottom 50 cap may also contain an opening, as shown. This bottom cap 50 may be configured with a curved, round, or chamfered edge so that the inferior plate closely matches the lower endplate of the intervertebral space. Like the other domed cap 40, this domed cap 50 may be eccentric or centric.

Figure 4A:
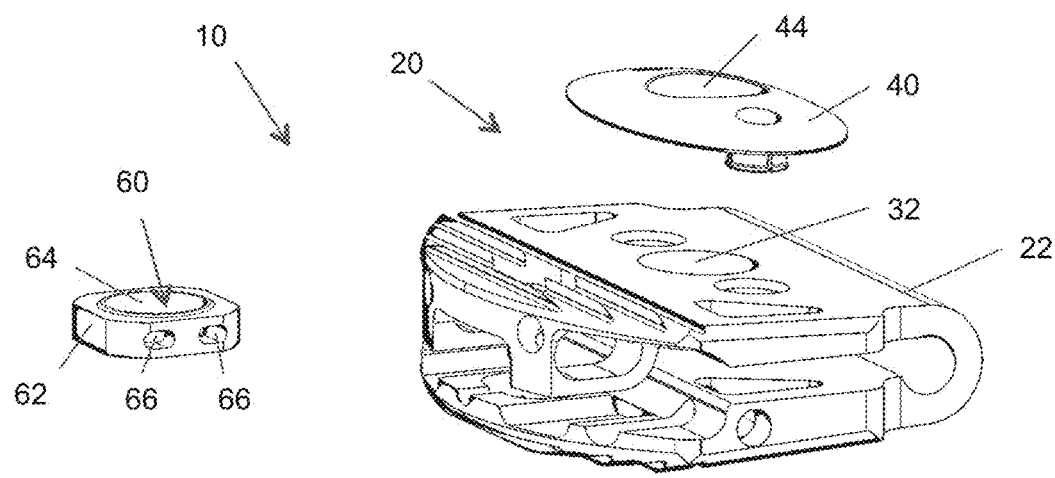

FIGS. 4A-4D illustrate an exemplary embodiment of another spine stabilization system that provides an implantable device similar to the one previously described for FIGS. 3A-3G, except that the domed cap may be provided without surface features. These surface features are optional, of course, and if so desired, could be included with the domed cap 40 of the present disclosure. In addition, as shown in FIG. 4A the system may include a fusion-enabling insert 60 that, when inserted into the main body 22, acts as a pillar to block or prevent compression.

The inferior plate 26 may also include an opening within which resides a bottom cap 50, as previously described. This bottom cap 50 may be configured with a curved, round, or chamfered edge so that the inferior plate closely matches the lower endplate of the intervertebral space. Like the other domed cap 40, this domed cap 50 may be eccentric or centric. In addition, this domed cap 50 for the inferior plate may 26 optionally include a through-hole 54 that can also be filled with bone graft material, bone cement, bone substitute material, bone hardening material, bone void filler, demineralized bone matrix, or other similar materials.

The domed caps 40, 50 may also comprise a bioactive coating for promoting fusion to anchor to bone tissue. This coating could contain a biological agent such as bone morphogenic protein (BMP), a peptide, a bone growth factor such as platelet derived growth factor (PDGF), stem cells, bone marrow, and platelet rich plasma (PRP), to name a few examples.

Figure 4B:
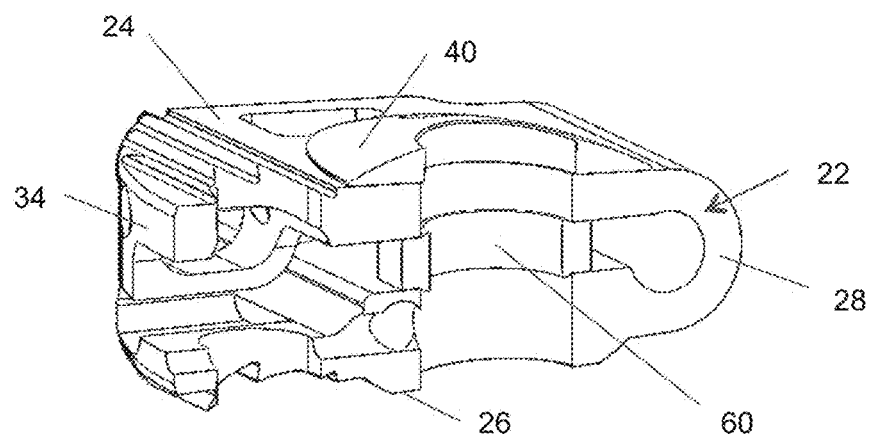
Figure 4C:
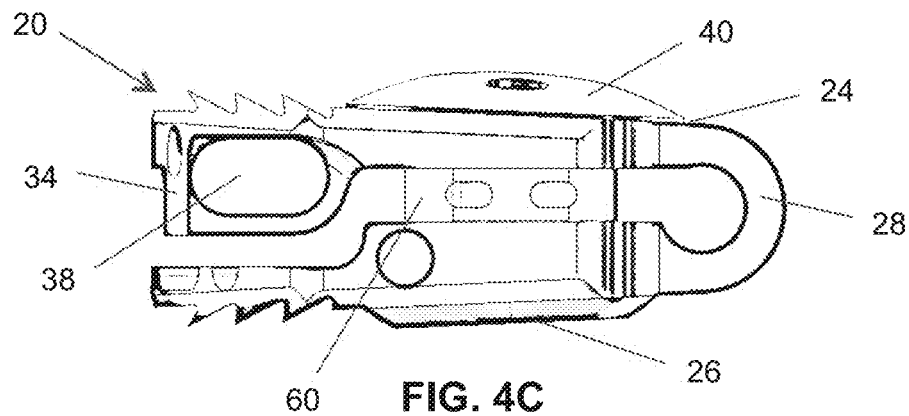
Figure 4D:
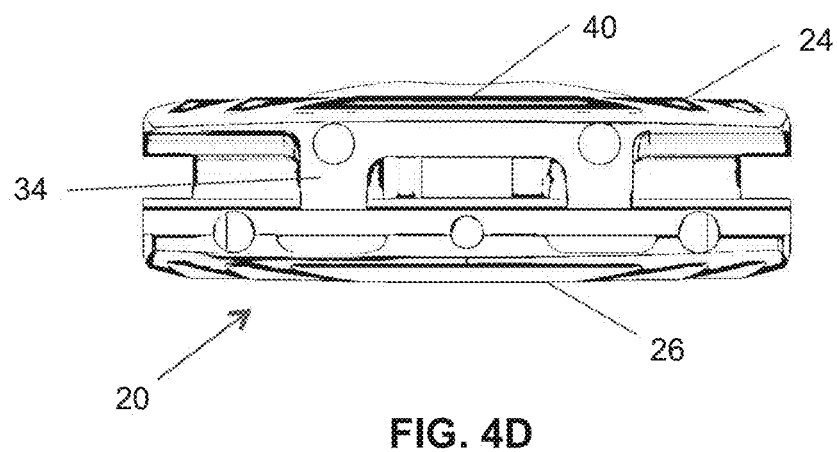

FIG. 4B illustrates a partial cutaway view of the spine stabilization device of FIG. 4A, showing the close fit between the insert 60 and the main body 22 when placed between the superior 24 and inferior 26 plates. This close fit is also seen in FIG. 4C which illustrates a side view of the spine stabilization device of FIG. 4A. As FIG. 4D illustrates, a front view of the spine stabilization device of FIG. 4A shows that the insert 60 can be inserted so as to reside entirely inside the main body itself and does not extend out of the main body 22.

Figure 5A:
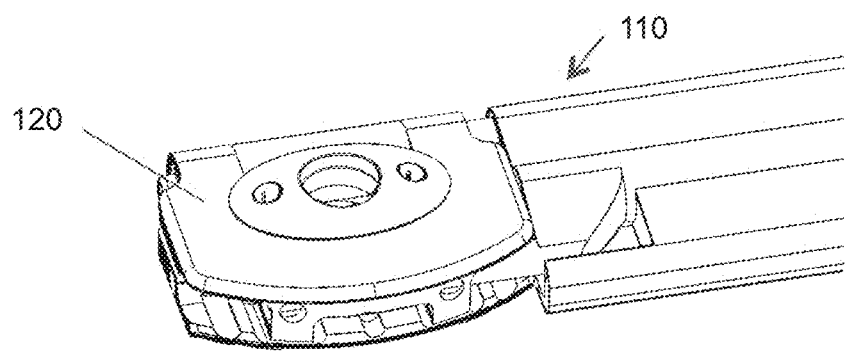
FIGS. 5A-5C illustrate a method of using a trial to assess the anatomical site for implantation in a lateral approach.
Figure 5B:
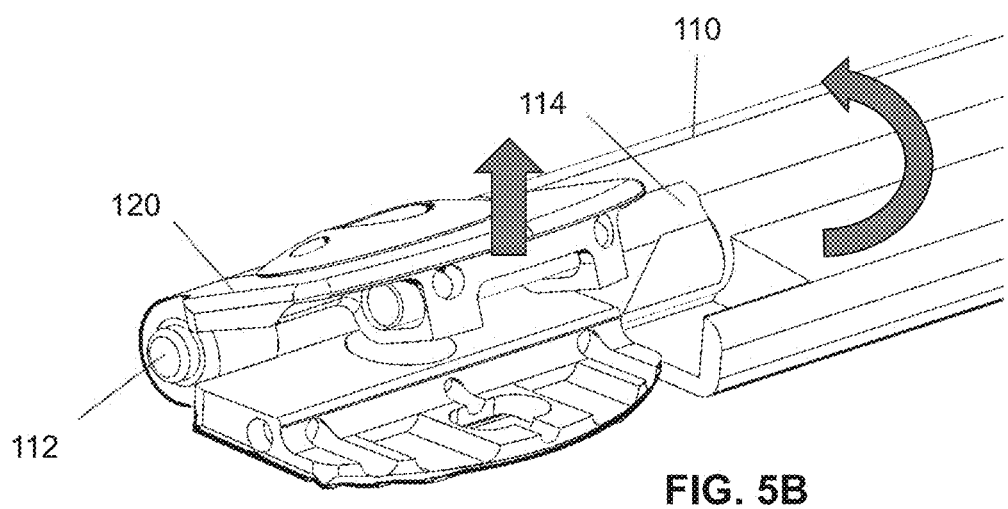
Figure 5C:
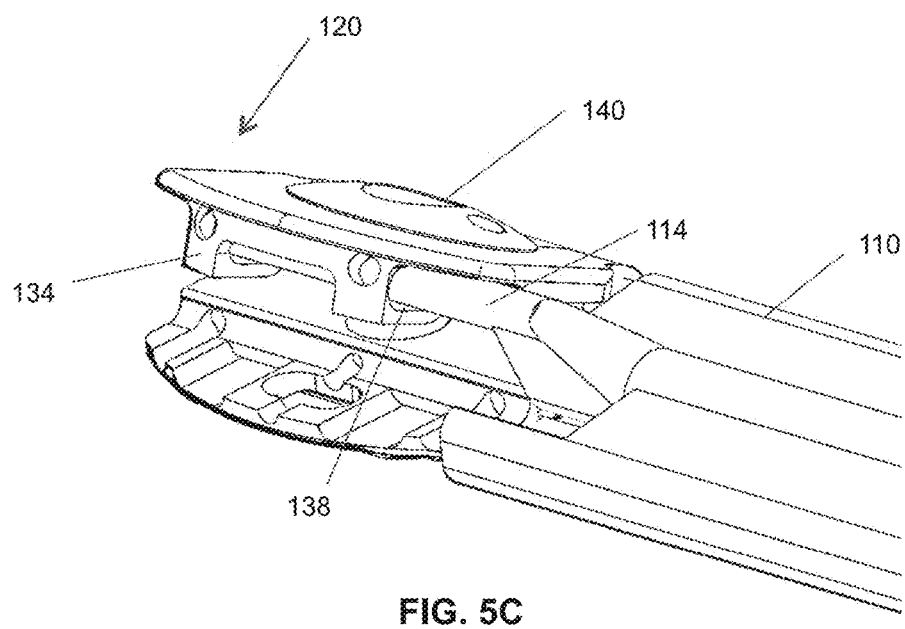

FIGS. 5A-5C illustrate a method of using a trial 120 to determine the morphological profile of the intervertebral space, and assess the anatomical site for implantation in a lateral approach. As shown in FIG. 5A, a trial 120 similar to the spine stabilization device of FIGS. 3A and 4A is attached to an inserter tool. Trial 120 shares similar structural features as spine stabilization device 20, with the same features having the same reference number following the prefix "1".

As FIG. 5B shows, the inserter tool 110 may comprise a stationary arm 112 and a movable arm 114 that engage the tool-engaging openings 138 of the trial 120. The insertion tool 110 may be configured so that the movable arm 114 is operable from the handle end such that the user can control the movement of the arm as indicated by the arrows. FIG. 5C shows a different angular view as the movable arm 114 is raised thereby causing the superior plate 124 to be lifted or extended up. The trial 120 and these steps allow the user to assess the morphological profile of the intervertebral space, examine the form-fit of the domed cap to be used on the spine stabilization device, footprint size and angulation. Any adjustments can then be made prior to implantation.

Figure 6A:
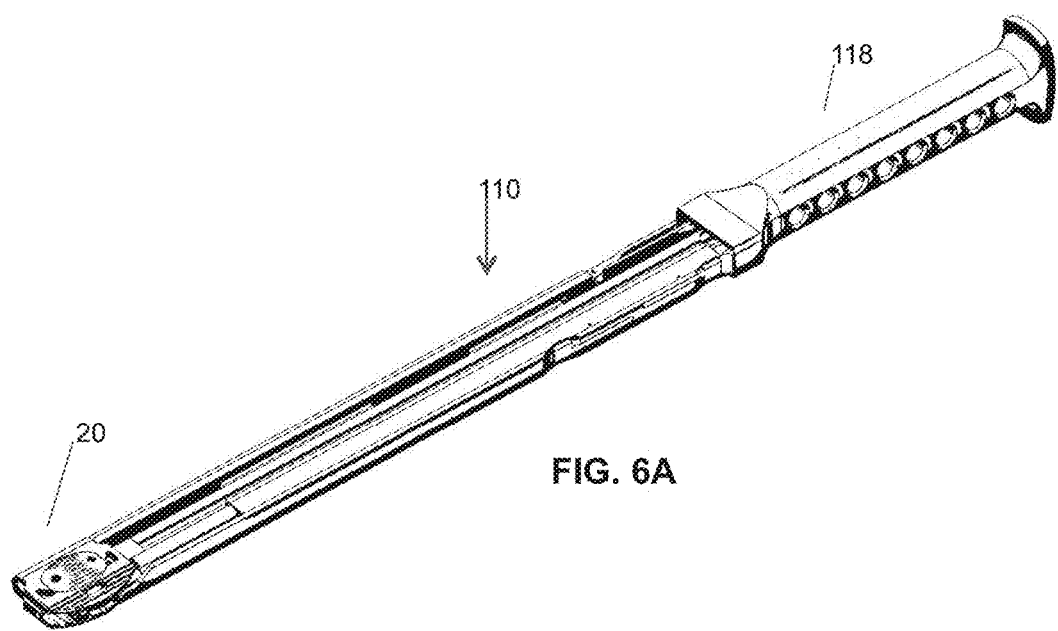
FIGS. 6A-6G illustrate a method of inserting the spine stabilization device of FIG. 4A in a lateral approach using exemplary embodiments of insertion instruments of the present disclosure.
Figure 6B:
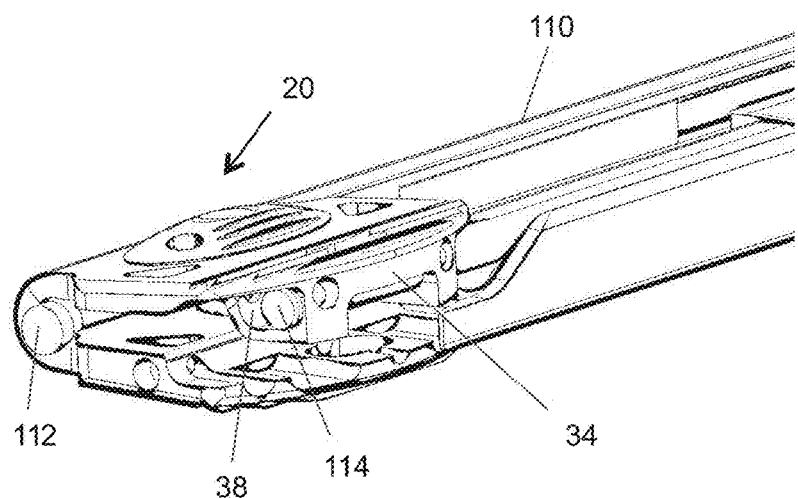
Figure 6C:
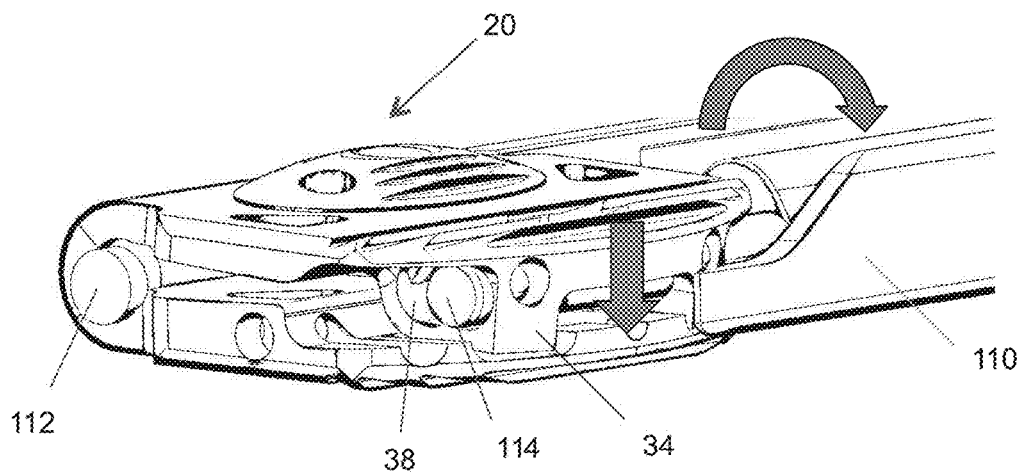

FIGS. 6A-6H illustrate a method of inserting the spine stabilization device 20 of FIG. 4A in a lateral approach. After trialing, the trial 120 may be removed from the insertion tool 110 and replaced with the actual spine stabilization device 20, complete with the domed cap 40 of choice, as shown in FIG. 6A. As the partial cutaway view of FIG. 6B and the side perspective view of FIG. 6C shows, the stationary arm 112 may extend in the hinged portion of the main body 22, while the movable arm 114 extends through the tool-engaging opening 38 in the undermounted panel 34 of the superior plate 24.

Figure 6D:
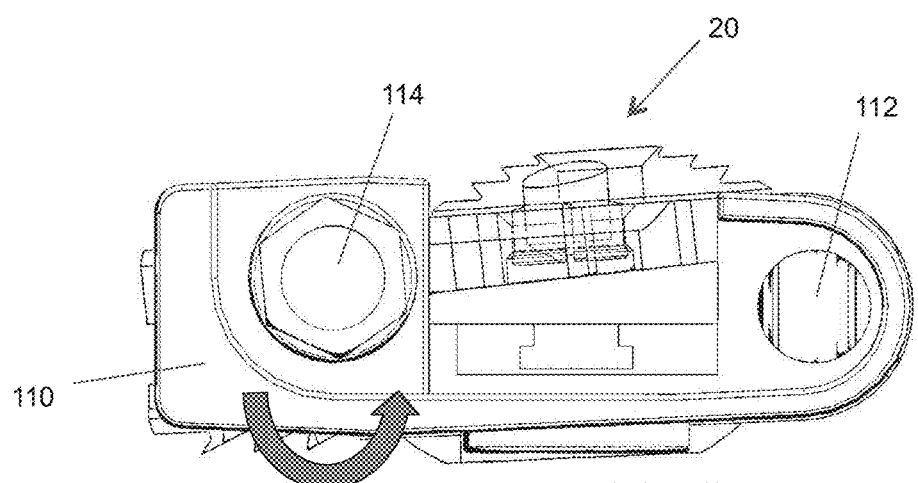

FIG. 6B shows the device 20 in a neutral position. To compress the main body 22 for insertion, the movable arm 114 may be lowered in the direction of the arrows as shown in FIGS. 6C and 6D. For example, the main body 22 may be compressed in a range from approximately 2 to 12 degrees, without limitation, such as 5 to 6 degrees, for insertion of the spine stabilization device 20.

Figure 6E:
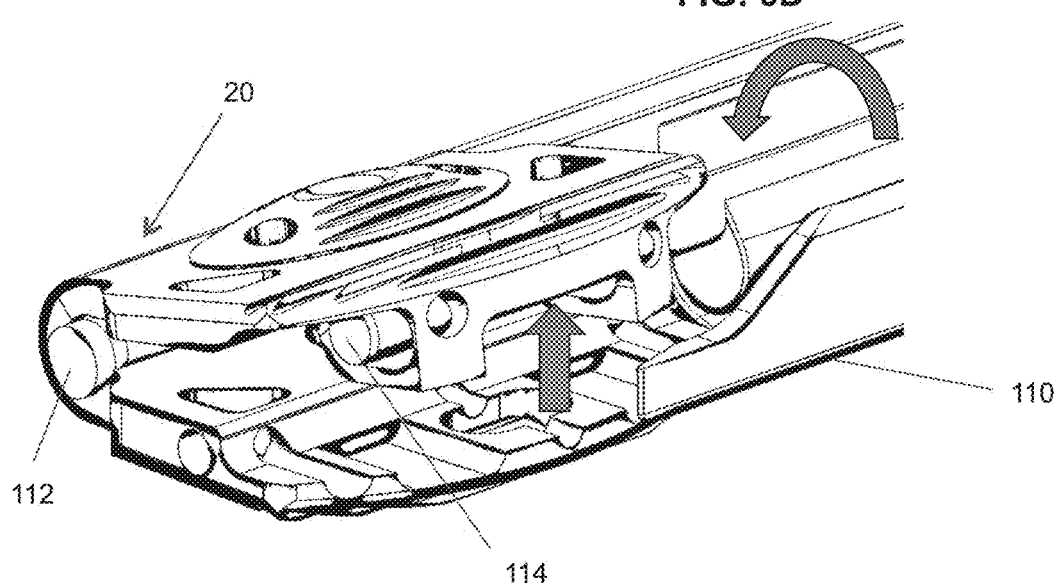
Figure 6F:
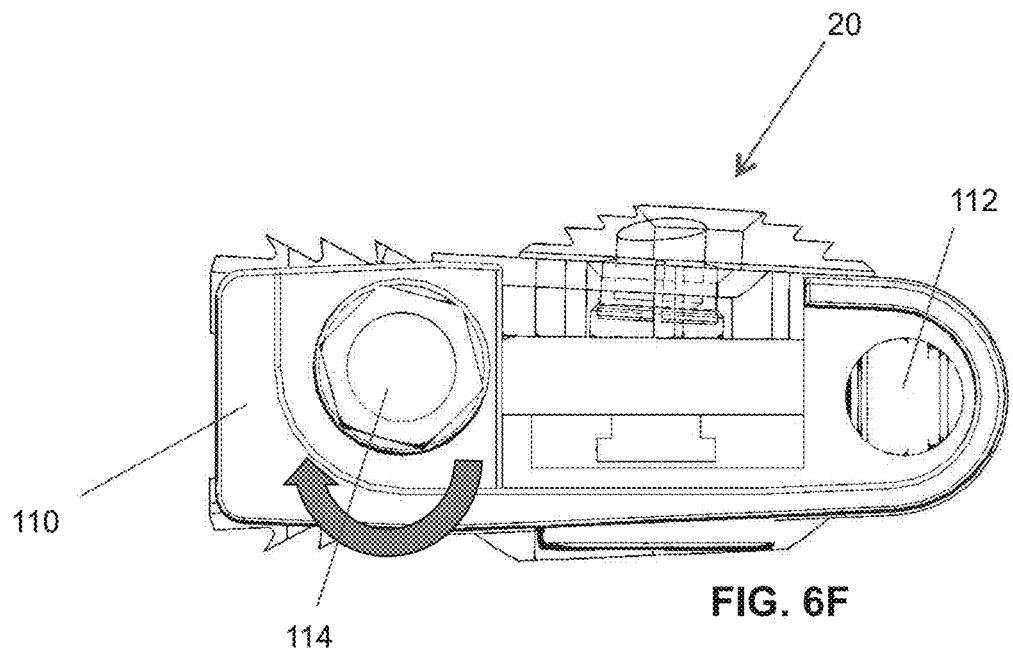

If distraction is desired, such as for lodortic alignment, the movable arm 114 would be raised upward in the direction of the arrows as shown in FIGS. 6E and 6F. Such movement would cause the superior plate 24 to be raised or distracted. For example, the angle of distraction may lie in a range from approximately 2 to 12 degrees, without limitation, such as approximately 3 to 5 degrees. Of course, these ranges are merely exemplary and are not intended to be limiting.

Figure 6G:
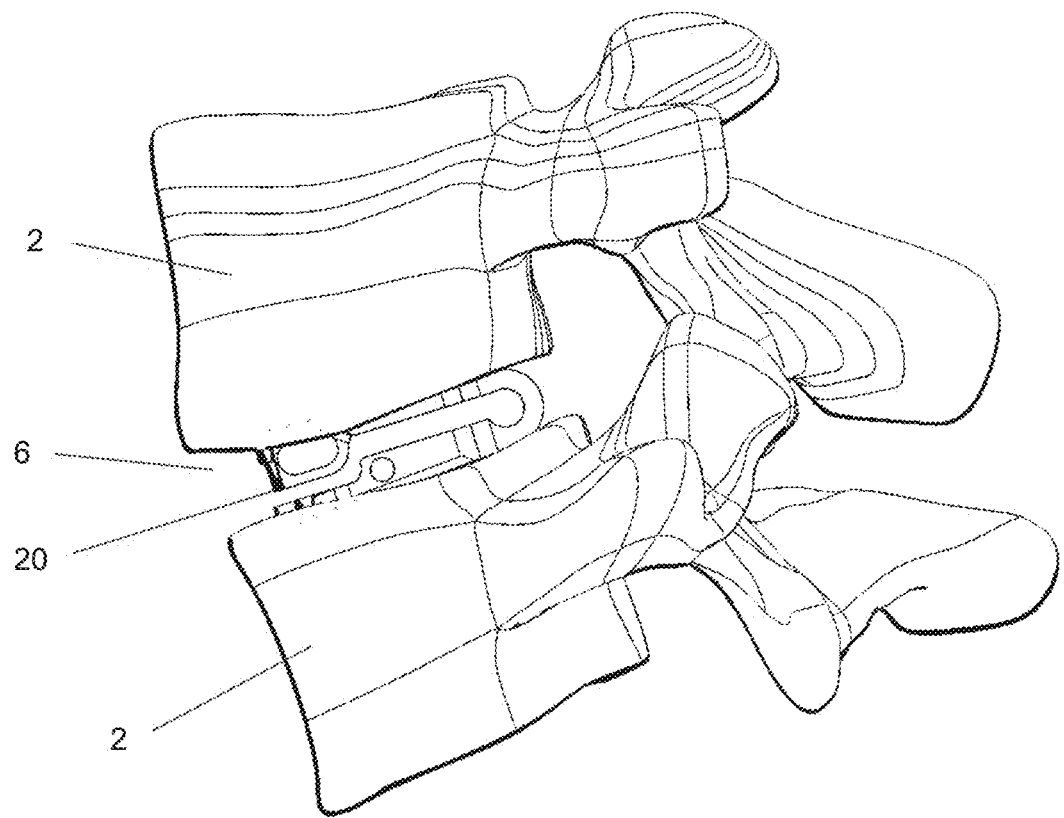

FIG. 6G shows the spine stabilization device 20 fully implanted within the intervertebral space 6 and seated securely between the intervertebral bodies 2. As illustrated, the spine stabilization device 20 is intended to be inserted entirely within the space 6, does not extend beyond the borders of the vertebral bodies 2 and does not require additional external fixation elements. In this mode, the spine stabilization device 20 serves as a stand-alone dynamic stabilization device. In the present example, the device is used in the lumbar spine. However, it is contemplated that the devices of the present disclosure may be configured and sized to be used in the thoracic and cervical spine if so desired.

Figure 7A:
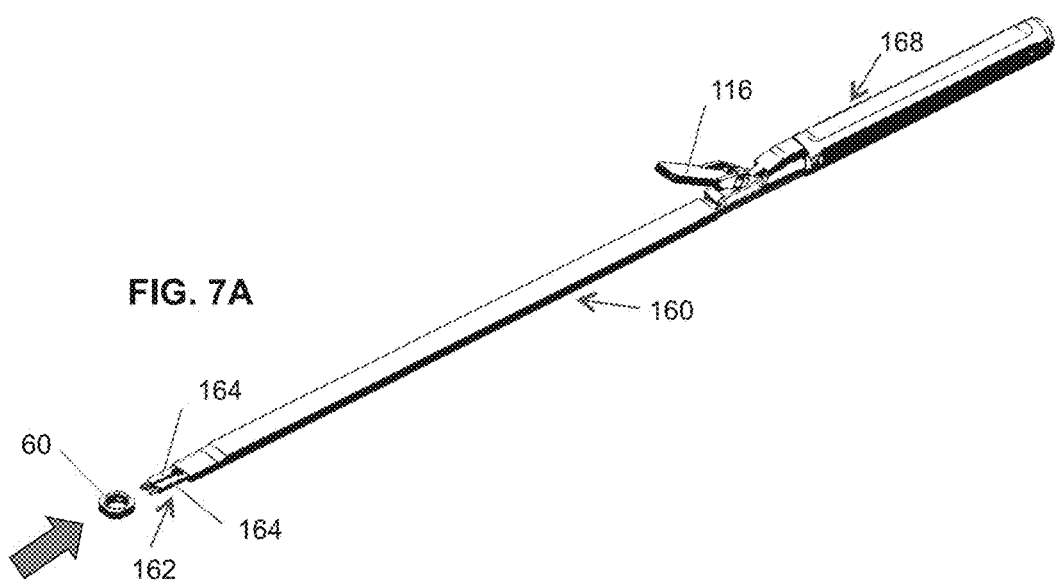
FIGS. 7A-7E illustrate a method of inserting a fusion-enabling insert into the spine stabilization device of FIG. 6G in a lateral approach using exemplary embodiments of insertion instruments of the present disclosure.
Figure 7B:
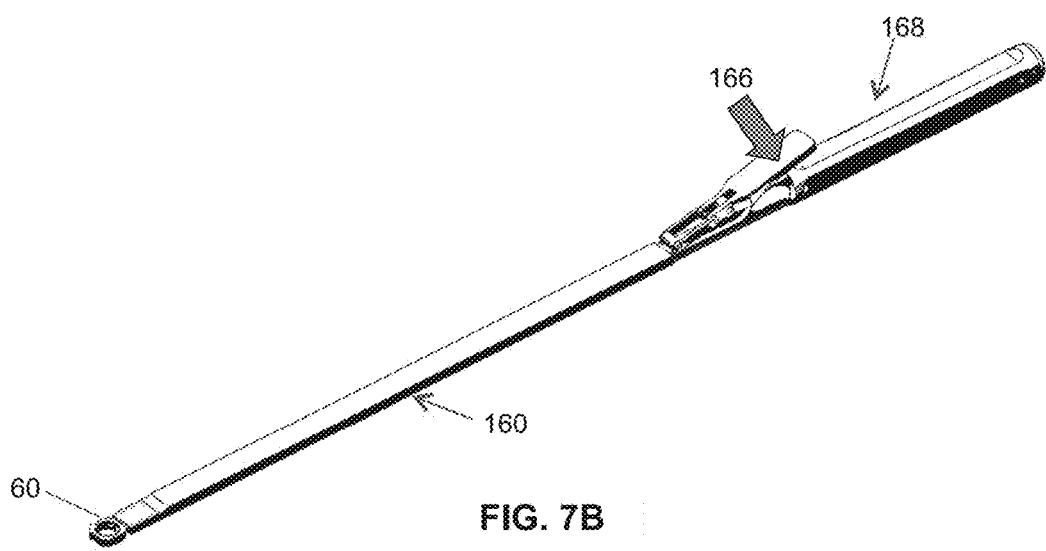

To convert the dynamic stabilization device into a fusion-enabling device, a blocking insert 60 may be placed within the main body 22 to prevent compression. FIGS. 7A-7E illustrate a method of inserting a fusion-enabling insert 60 into a spine stabilization device 20 similar to FIG. 6G in a lateral approach. The fusion-enabling insert 60 may first be attached to an insert delivery instrument 160. The instrument may comprise an operable end 162, a handle 168, a catch and release switch 166, and arms 164 that extend into the tool-engaging holes 66 of the insert 60. As shown in FIG. 7A, the insert may be placed onto the arms of the insert delivery instrument. Once the insert 60 is on the arms 164, the catch and release switch 166 may be activated in the direction of the arrow shown in FIG. 7B. To release the insert, the user would simply need to reactivate the switch 166.

Figure 7C:
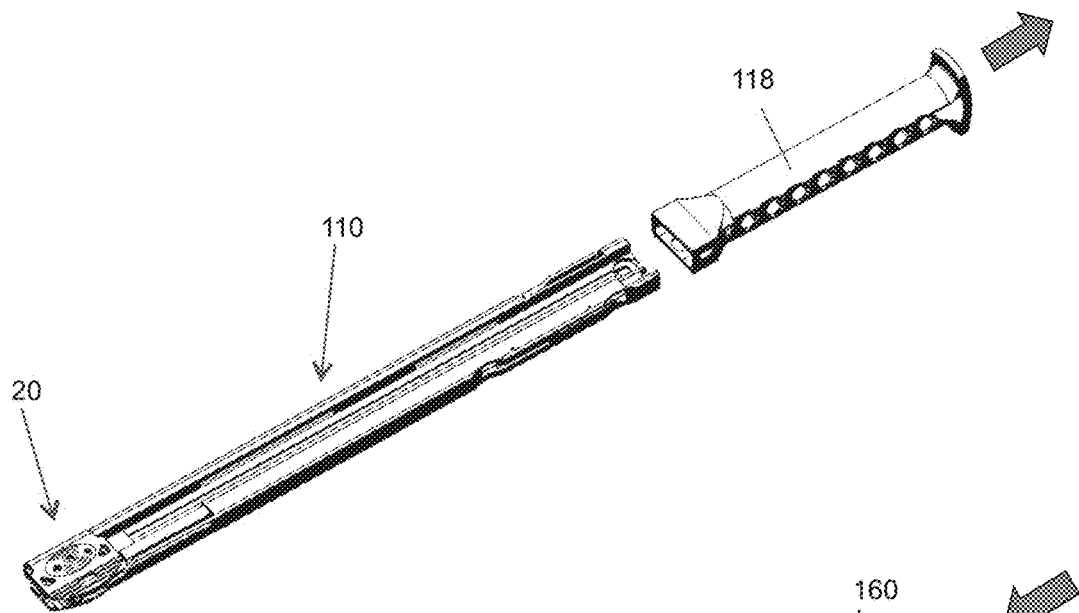
Figure 7D:
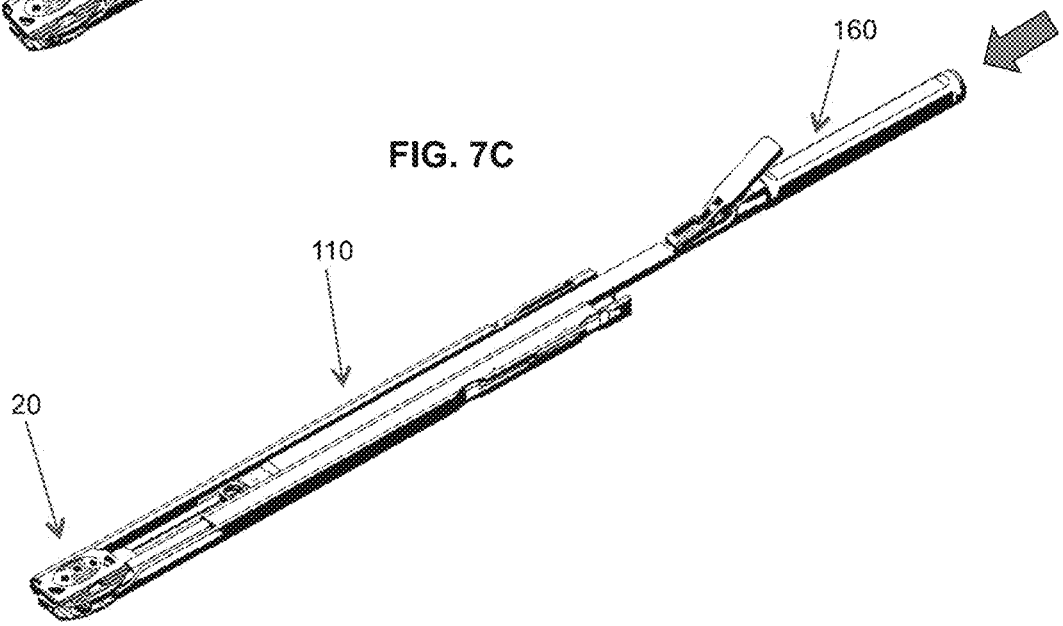
Figure 7E:
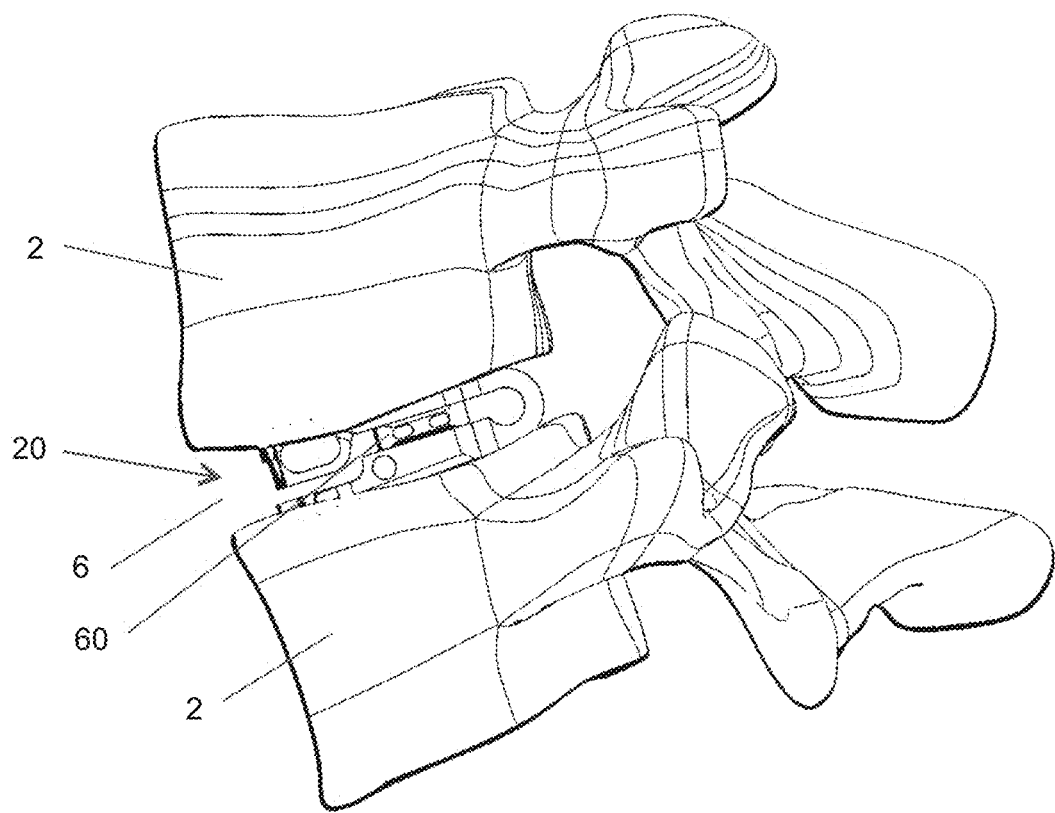

Next, as shown in FIG. 7C, the spine stabilization device 20 for implantation is attached to the inserter tool 110 similar to the process previously described at FIG. 6A. Once the spine stabilization device is properly positioned in the intervertebral space, the handle portion 118 of the inserter tool 110 is removed as indicated by the arrow shown in FIG. 7C. Then, the insert delivery instrument 160 is slid into the inserter tool 110, as shown in FIG. 7D. The insert 60 may be placed within the main body 22, the insert delivery instrument 160 removed, and then the inserter tool 110 removed to leave behind the spine stabilization device 20 in a fusion-enabling mode, as shown in FIG. 7E.

Figure 8A:
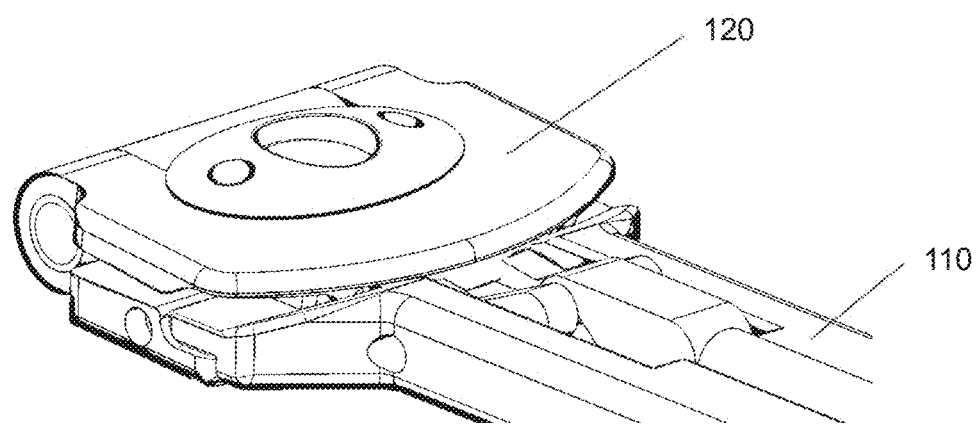
FIGS. 8A-8C illustrate a method of using a trial to assess the anatomical site for implantation in a ventral approach.
Figure 8B:
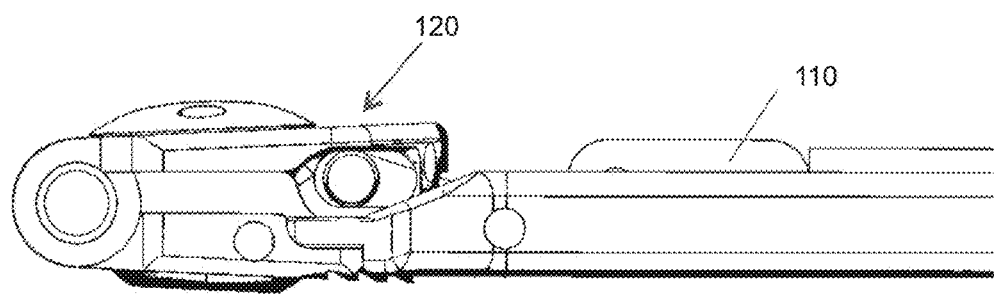
Figure 8C:
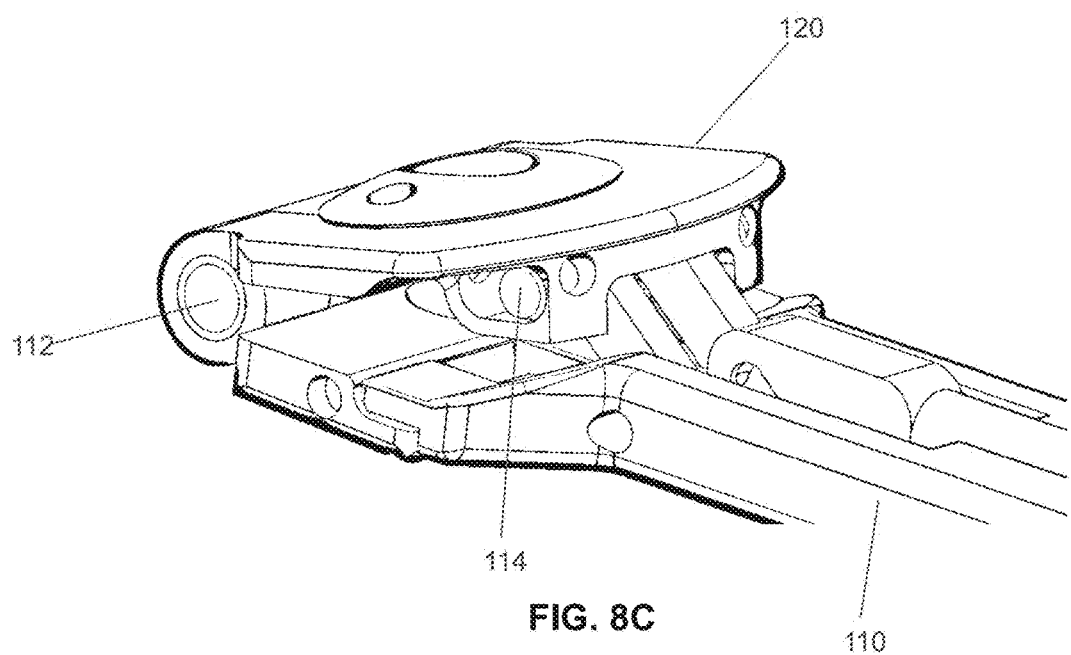

As mentioned, the present device 20 may be inserted in either a lateral or ventral approach. FIGS. 8A-8C illustrate a method of using a trial to determine the morphological profile of the intervertebral space, and assess the anatomical site for implantation in a ventral approach. To insert the devices of the present disclosure by a ventral approach, the process of trialing may again precede the actual implantation steps. As shown in FIGS. 8A-8C, the trial 120 may be used to examine dome form-fit, footprint size and angulation. Once those parameters are defined, the user can then determine what configuration the final device needs to have.

In a ventral approach, another insertion tool may be provided that allows the superior plate to be lifted from the front, as indicated by the arrow in FIG. 8C. The ventral insertion tool may have a single movable arm along with a rest plate with extending pins that are inserted into the inferior plate for stability.

FIGS. 9A-9F illustrate a method of inserting the spine stabilization device 20 of FIG. 4A in a ventral approach. After trialing, the actual spine stabilization device 20, complete with the domed cap 40 of choice, may be attached to the ventral delivery instrument 130 as shown in FIGS. 9A-9D. As shown, the stabilizing pins 132 of the ventral delivery instrument 130 may extend in the openings of the inferior plate of the main body, while the movable pins 134 may be positioned to extend through the tool-engaging openings 38 in the undermounted panel 34 of the superior plate.

Figure 9A:
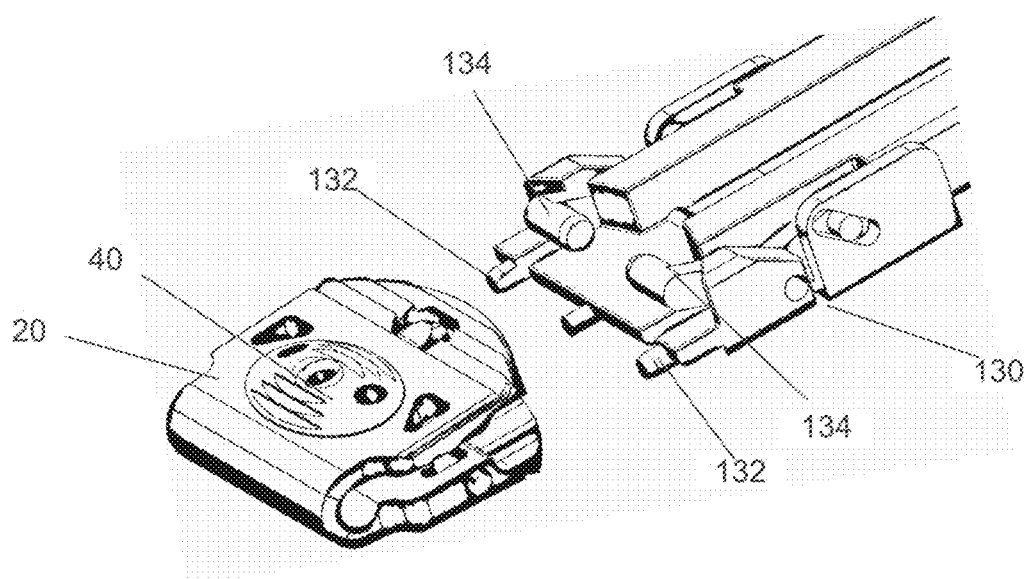
FIGS. 9A-9F illustrate a method of inserting the spine stabilization device of FIG. 4A in a ventral approach using exemplary embodiments of insertion instruments of the present disclosure.
Figure 9B:
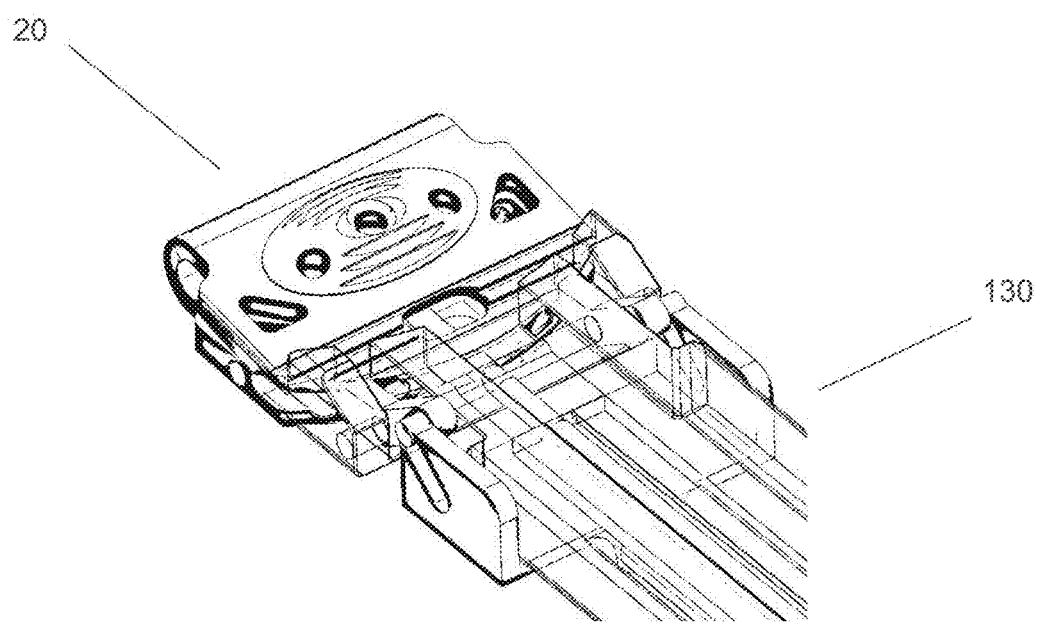
Figure 9C:
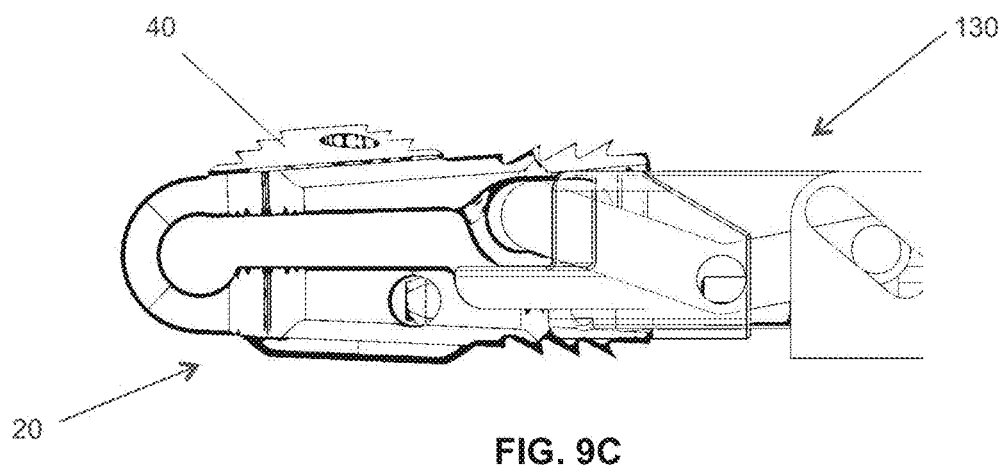
Figure 9D:
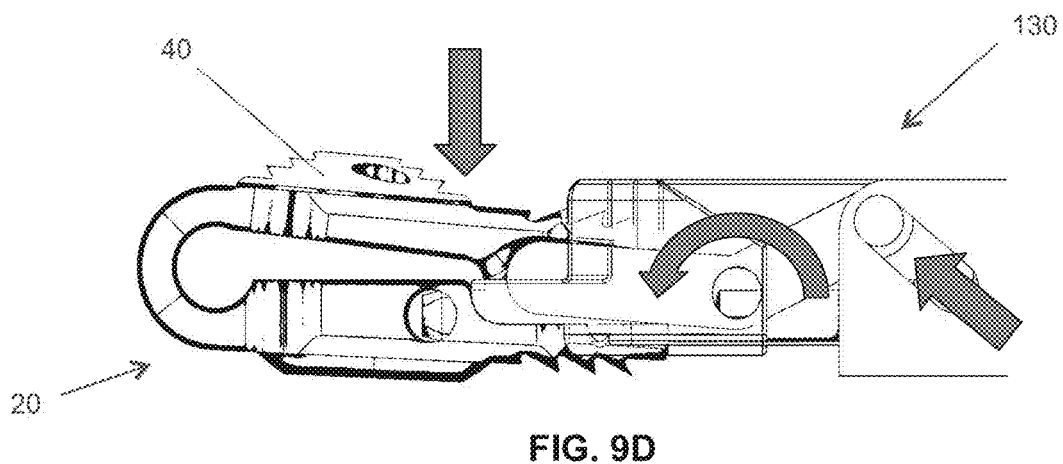

FIGS. 9A-9C show the device in a neutral position. To compress the main body 22 for insertion, the movable pins 134 may be lowered in the direction of the arrows as shown in FIG. 9D. The main body 22 may be compressed for insertion of the spine stabilization device 20.

Figure 9E:
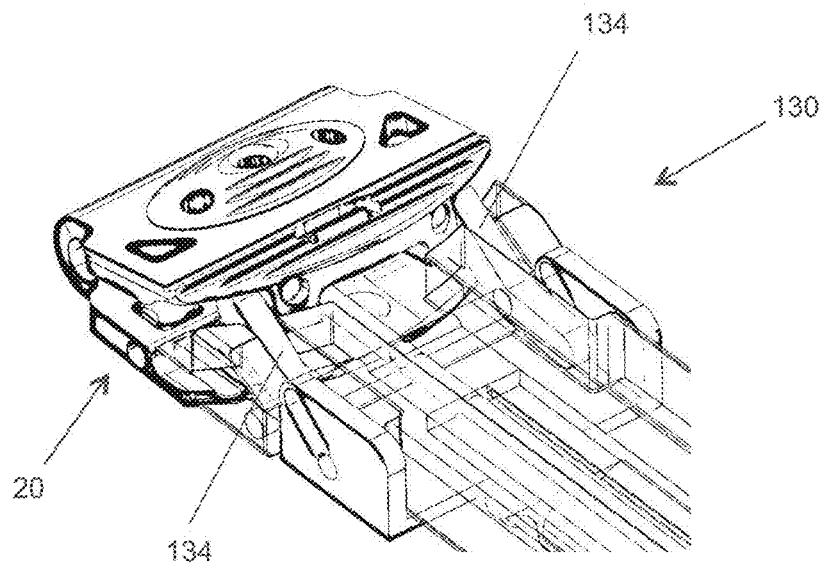
Figure 9F:
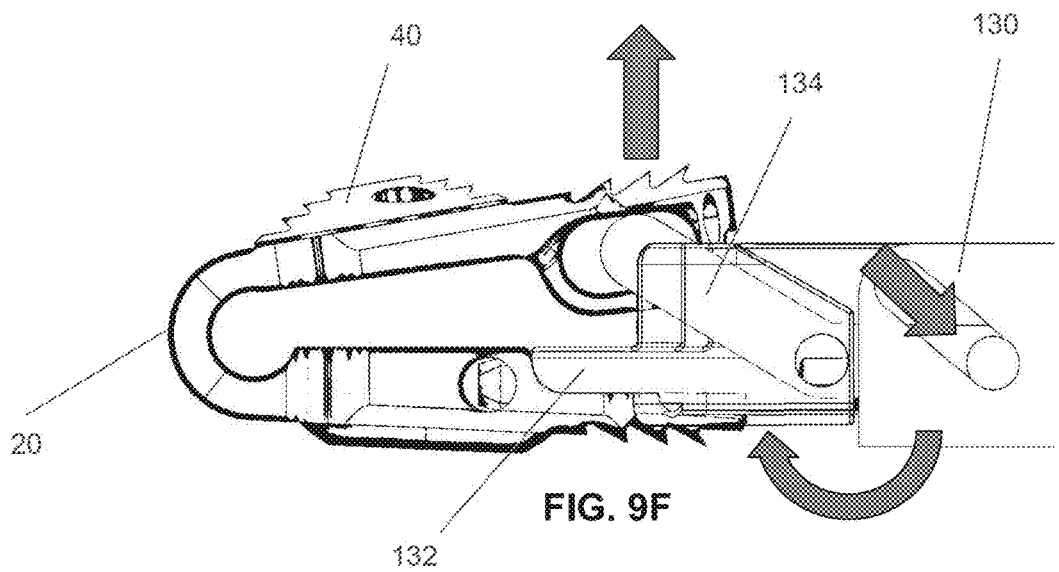

If distraction is desired, such as for lodortic alignment, the movable pin would be raised upward in the direction of the arrows as shown in FIGS. 9E and 9F. Such movement would cause the superior plate 24 to be raised or distracted. Thereafter, an insert 60 may be placed in between to adjust the height of the device as well as the angle of the device (lodortic curvature) to achieve sagittal balance. Accordingly, inserts 60 provided by the present disclosure have varying heights and/or angles.

Figure 10A:
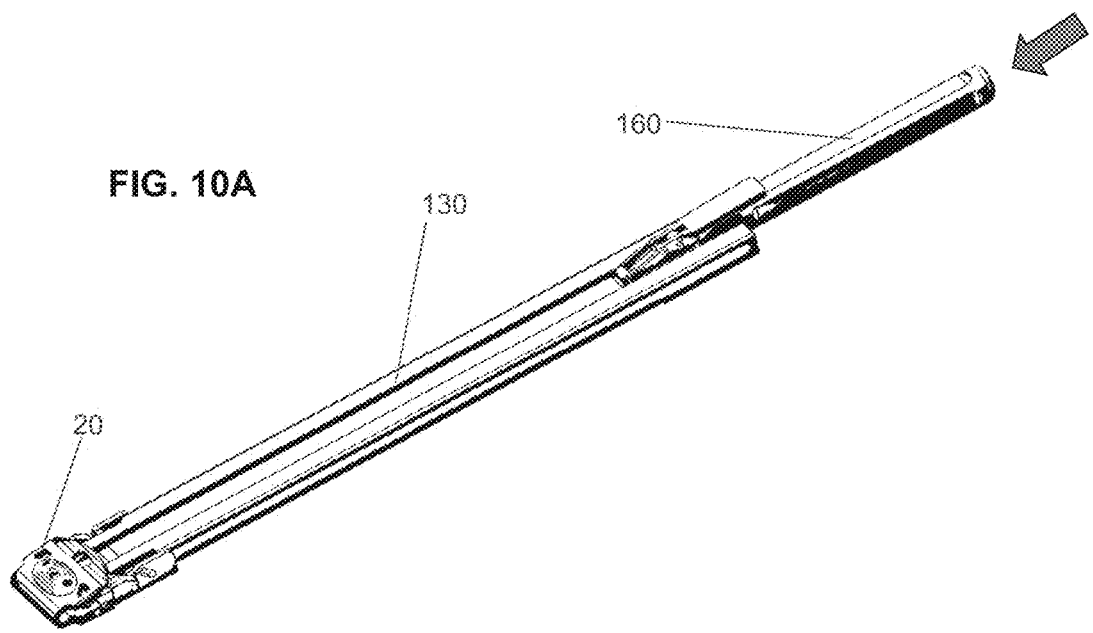
FIGS. 10A and 10B illustrate a method of inserting a fusion-enabling insert into the spine stabilization device of FIG. 9F in a ventral approach using exemplary embodiments of insertion instruments of the present disclosure.
Figure 10B:
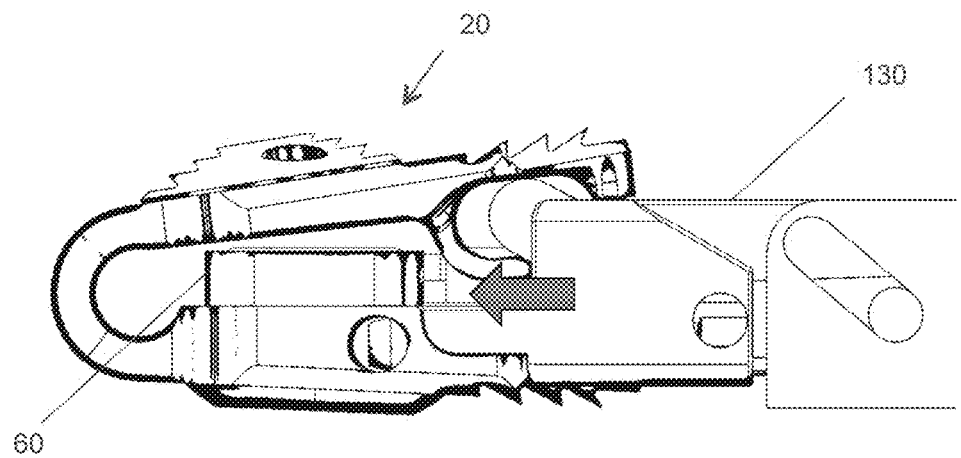

FIGS. 10A and 10B illustrate a method of inserting a fusion-enabling insert into the spine stabilization device of FIG. 9F in a ventral approach. Similar to the method described above, the fusion-enabling insert 60 may be positioned within the main body 22 of the spine stabilization device by sliding an insert 60 along with the insert delivery instrument 160 into the ventral delivery instrument 130 and releasing the insert 60 into the main body of the device 20.

The devices are configured to be stand-alone devices. However, it is also possible to utilize these devices with a posterior fixation device or system for total 360 degree stabilization. Suitable posterior fixation devices may include interspinous stabilization devices such as the one described in U.S. Pat. Nos. 5,645,599 and 7,922,750, to name a few examples.

In some embodiments, the devices may be configured for use with fixation screws. For instance, the compression-blocking insert may be configured for attachment to the vertebral bodies with fixation screws. In one embodiment, the inserts may comprise an attachment plate for receiving the fixation screws. In another embodiment, the fixation screws may be attached to the main body.

Figure 11A:
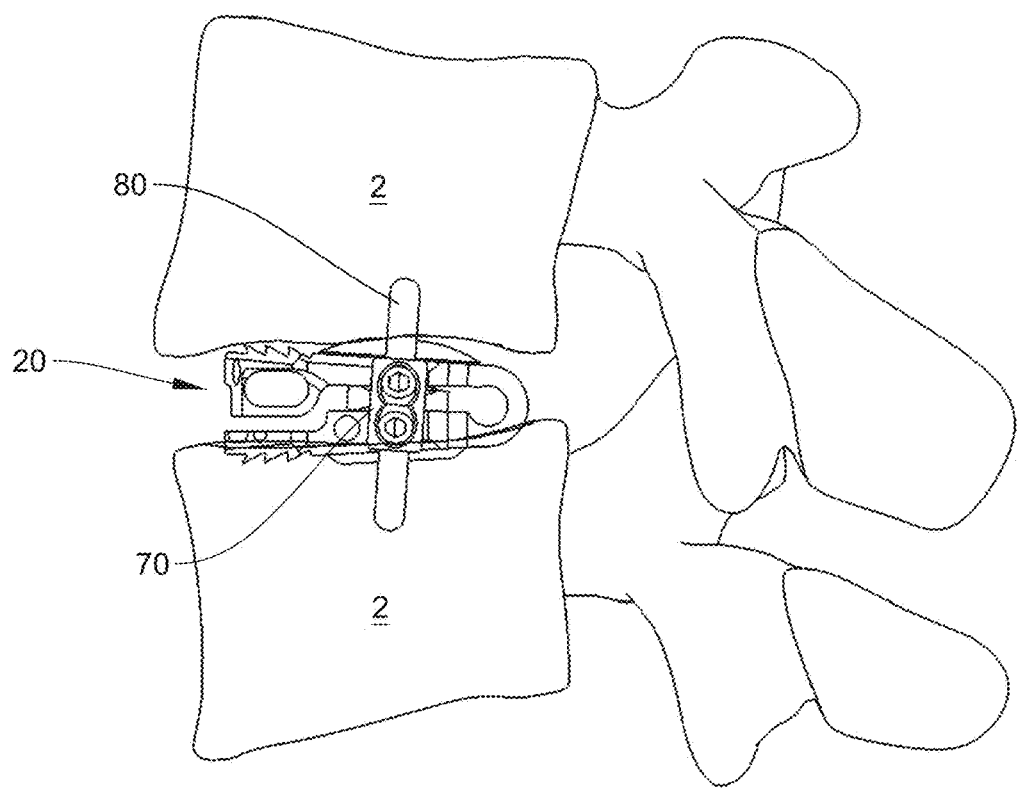
Figure 11B:
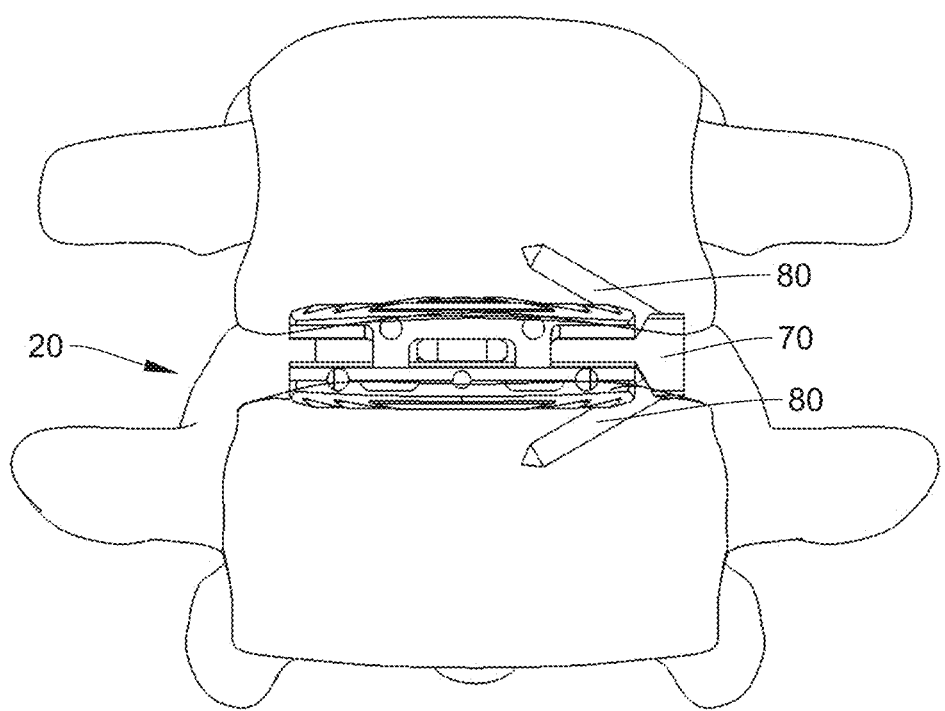
Figure 11C:
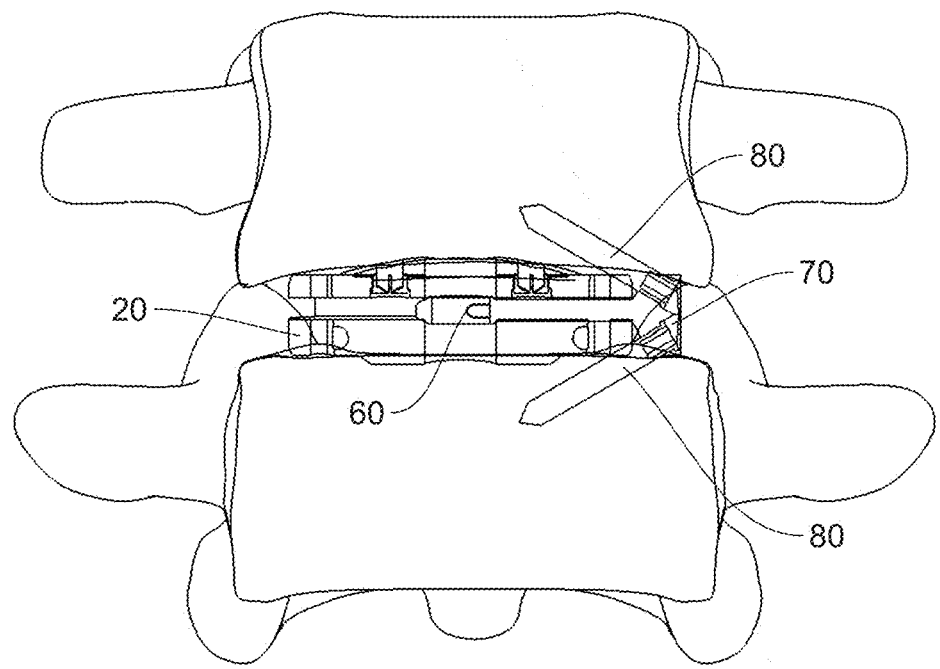

Turning now to the drawings, FIGS. 11A-11F illustrate another exemplary embodiment of a spine stabilization device of the present disclosure having a fusion-enabling insert configured for external fixation. As shown in FIGS. 11A-11C, the spine stabilization device 20 can be secured to the side of the vertebral bodies 2 with fixation screws 80. In the present embodiment, the insert 60 may extend into a screw holding block 70 that is configured to reside outside of the vertebral bodies 2. The screw holding block 70 would include screw holes for receiving the screws 80. The device 20 may be secured to the sides of the vertebral bodies 2, as shown.

Figure 11D:
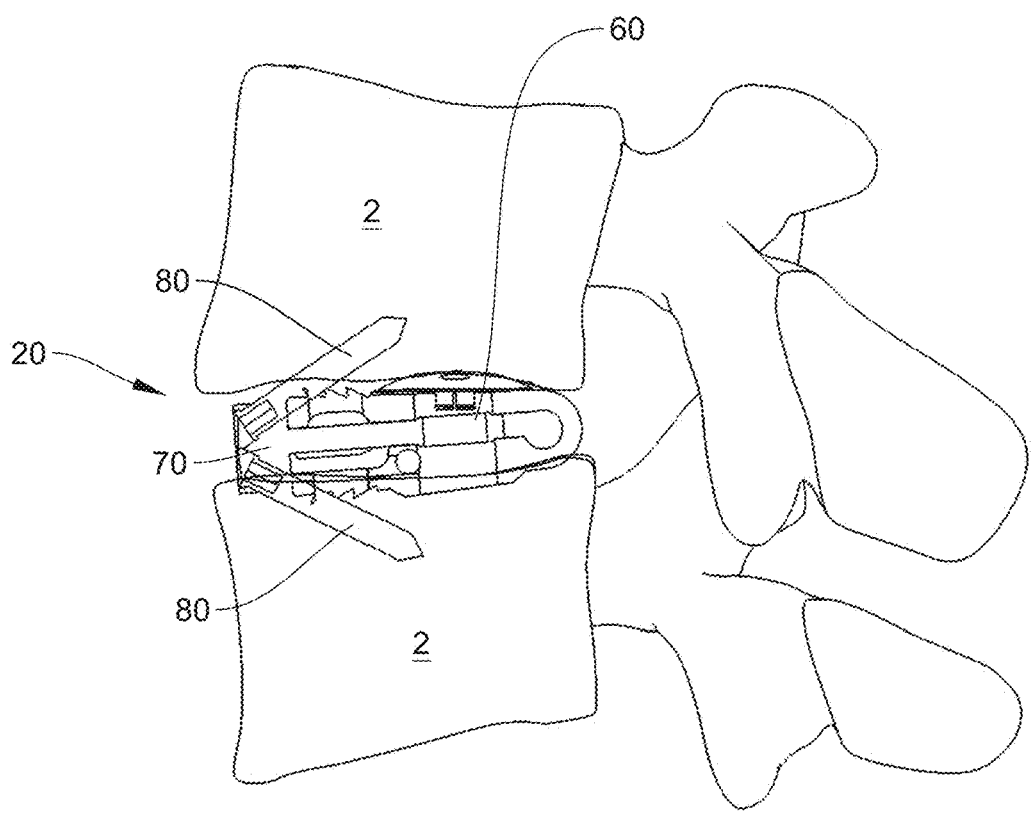
Figure 11E:
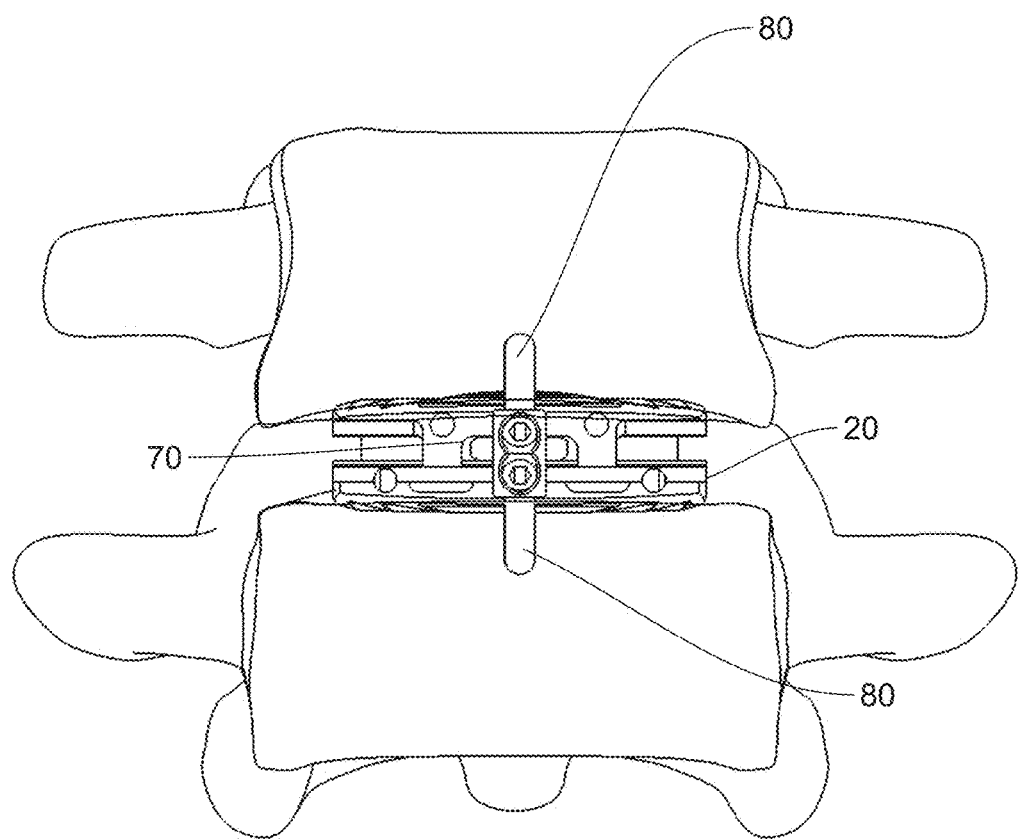
Figure 11F:
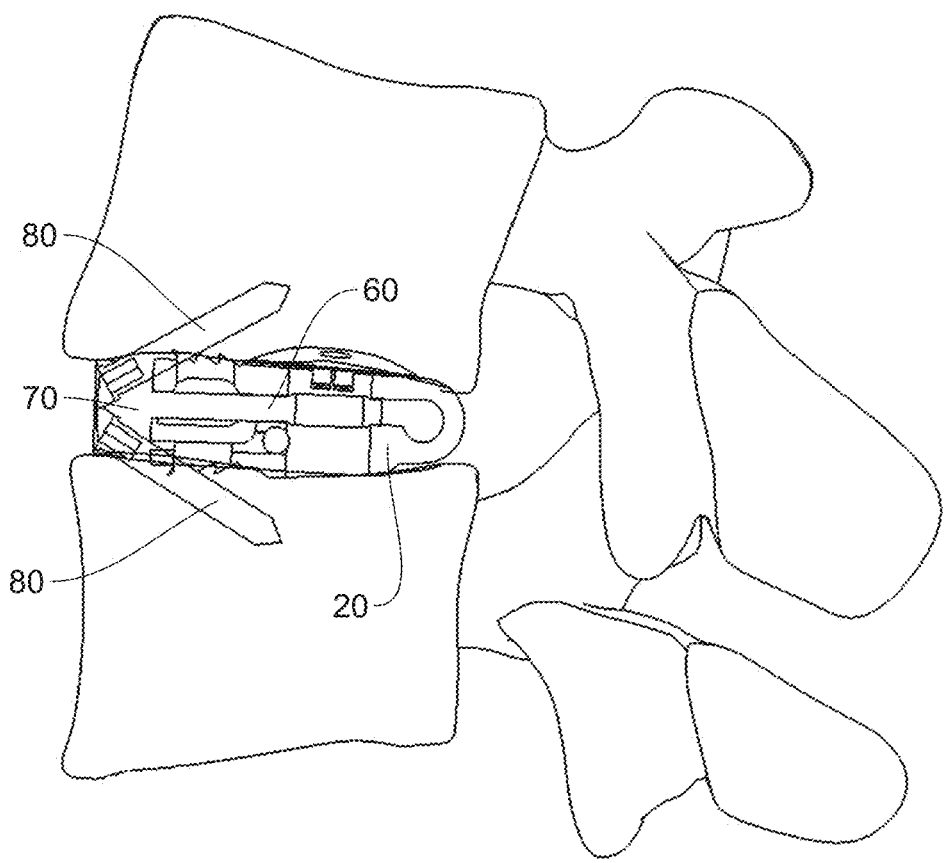

FIGS. 11D-11F show the same spine stabilization device 20 as above, but secured to the front of the vertebral bodies 2. By rotating the insert 60 90 degrees such that the screw holding block 70 extends toward the front of the spine, the entire construct may be secured using the same screws 80 to the front of the vertebral bodies 2, as shown.

Figure 12A:
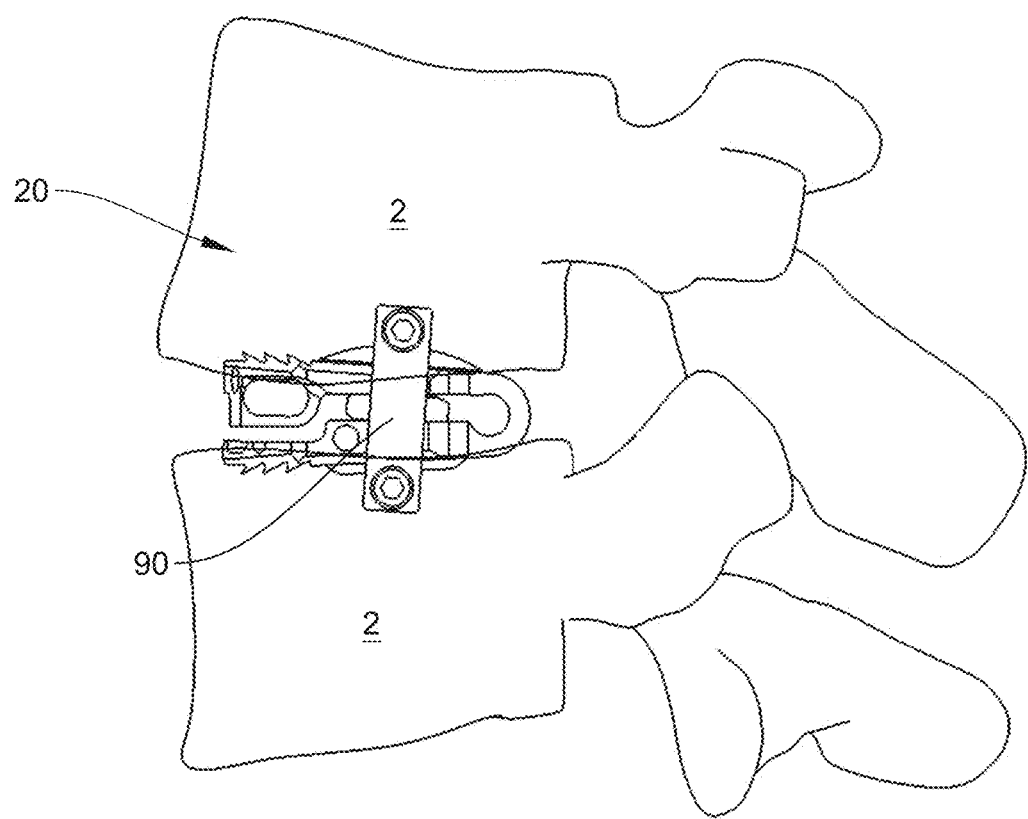
Figure 12B:
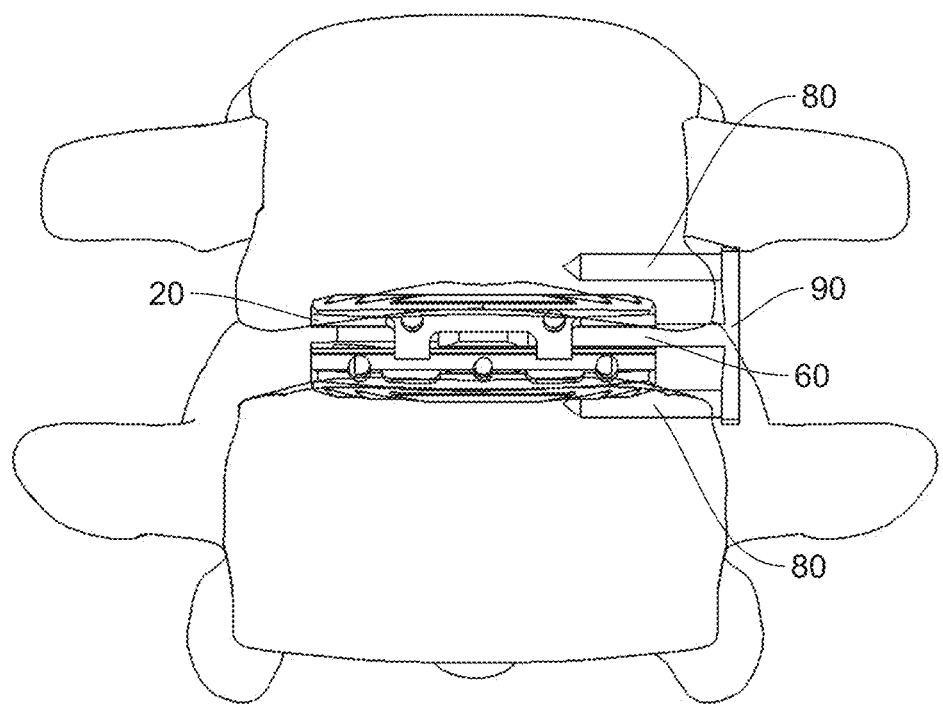

FIGS. 12A-12D illustrate still another exemplary embodiment of a spine stabilization device 20 of the present disclosure having a fusion-enabling insert configured for external fixation. FIGS. 12A and 12B show the spine stabilization device 20 secured to the side of the vertebral bodies 2. In the present embodiment, the insert 60 extends into an attachment plate 90 that resides outside the bodies 2, as shown. The entire construct may be secured with fixation elements like bone screw 80, through the attachment plate 90, and to the vertebral bodies 2.

Figure 12C:
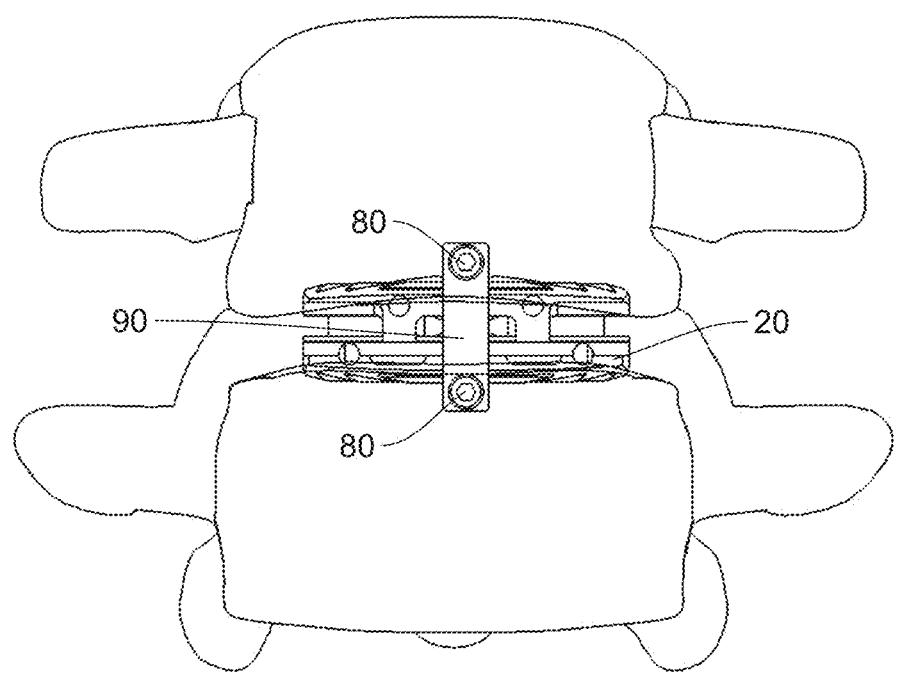
Figure 12D:
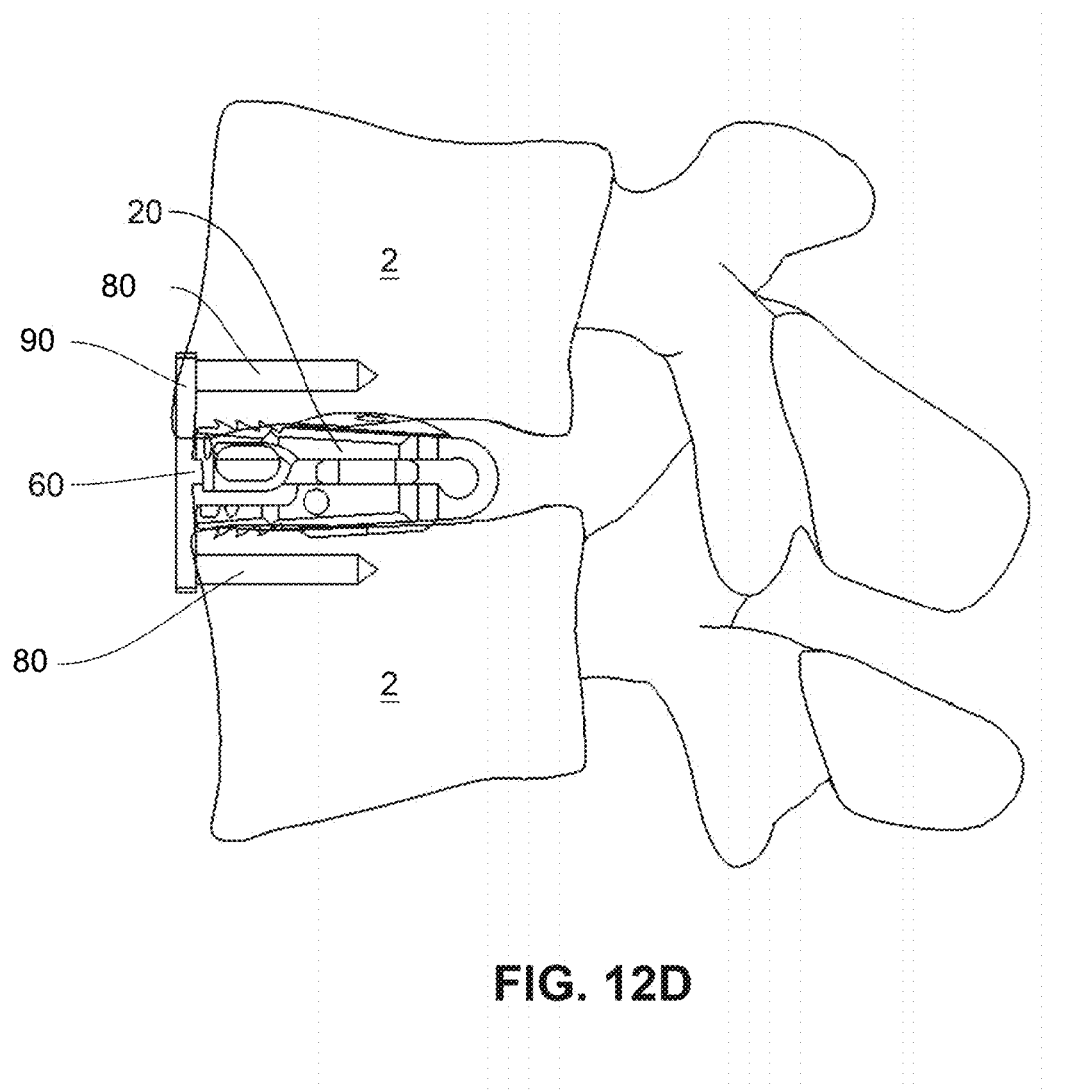

The insert 60 of FIGS. 12A and 12B may be rotated about 90 degrees to allow the device 20 to be secured to the front of the vertebral bodies 2, as shown in FIGS. 12C and 12D. show the spine stabilization device secured to the front of the vertebral bodies.

Figure 13A:
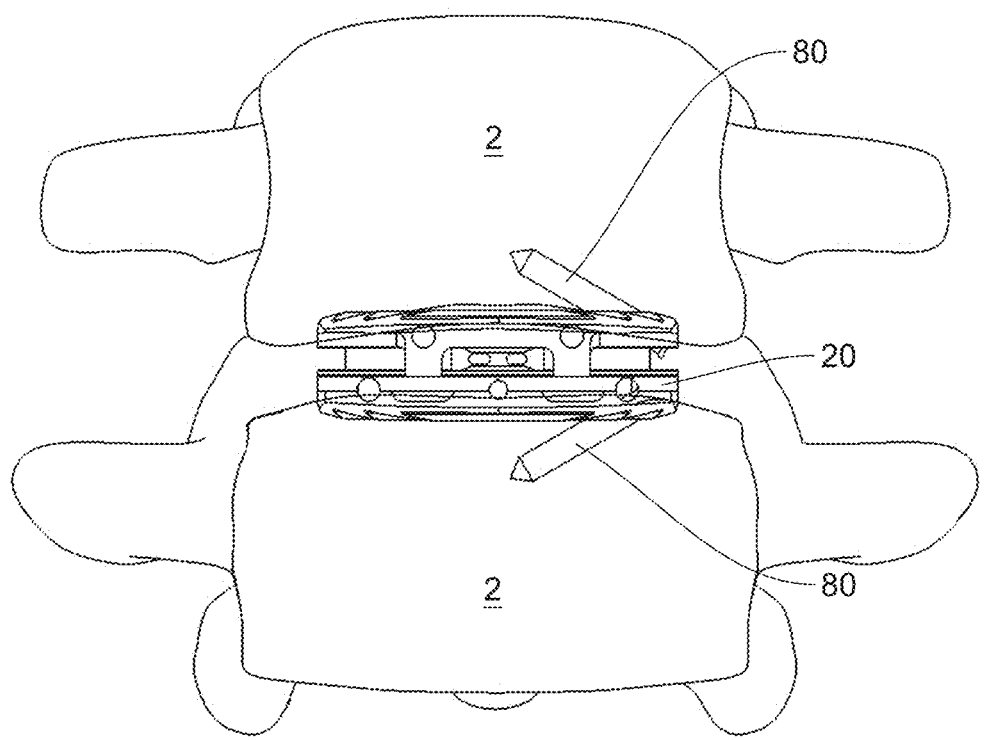
Figure 13B:
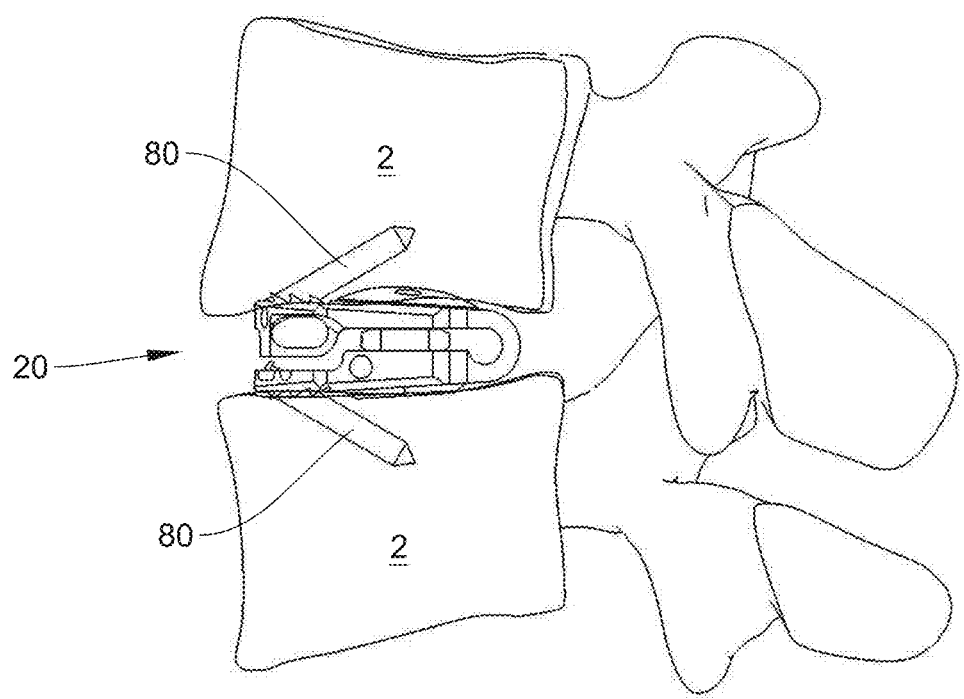

FIGS. 13A and 13B illustrate yet another exemplary embodiment of a spine stabilization device of the present disclosure configured for external fixation. In the present embodiment, the device 20 may simply be provided with screw holes to allow insertion of fixation elements or bone screw 80. Thus, in some cases, the device 20 may be directly secured to the endplates of the vertebral bodies 2, as shown, by inserting screws 80 through the device into the vertebral bodies 2 above and below the device 20.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A modular, implantable spine stabilization system comprising interchangeable components that can be assembled into a device that is customizable to match a morphology of an implant site and may be converted into a spine fusion enabling device, said system comprising:
    a main body having a superior plate having an opening extending therethrough, an inferior plate, and a flexible sidewall connecting the superior and inferior plates to define a closed end of the main body, the main body further including an open end opposite the closed end, and lateral side openings between the upper and lower plates;
    at least one domed cap comprising a domed top and a stem extending from the domed top and configured for engagement with the opening through the superior plate; and
    at least one insert configured for placement between the superior and inferior plates through at least one of the open end opposite the closed end or at least one of the lateral side openings to prevent compression of the main body.

2. The system of claim 1, wherein the at least one insert included with the system is rotatable within the main body.

3. The system of claim 2, wherein the at least one insert included with the system further includes a screw holding block for receiving screws to secure the device to vertebral bodies.

4. The system of claim 2, wherein the at least one insert included with the system further includes an attachment plate for securing the device to vertebral bodies.

5. The system of claim 4, wherein the attachment plate may be secured to a side of the vertebral bodies.

6. The system of claim 4, wherein the attachment plate may be secured to a front surface of the vertebral bodies.

7. The system of claim 1, wherein the at least one domed cap included with the system includes a through-hole.

8. The system of claim 7, wherein the opening of the superior plate and through-hole of the at least one domed cap are aligned to create a receiving channel when the domed cap is engaged with the superior plate.

9. The system of claim 8, further including bone graft material, bone cement, bone void filler, bone substitute material, bone hardening material, bone chips, or demineralized bone matrix for insertion into the receiving channel.

10. The system of claim 1, wherein at least one of the main body and domed cap includes surface features for anchorage to bone tissue.

11. The system of claim 10, wherein the surface features comprise teeth, ridges, spikes, or roughened surfaces.

12. The system of claim 1, wherein the superior plate has a panel extending from an underside thereof, the panel including at least one tool-engaging opening.

13. The system of claim 12, wherein the panel further includes a cutaway slot for allowing passage of the at least one compression-blocking insert into the main body.

14. The system of claim 1, wherein the at least one domed cap may be eccentric or centric, and is attachable to the superior plate in different orientations.

15. The system of claim 1, further including at least one cap configured to engage the inferior plate.

16. The system of claim 1, wherein the at least one domed cap comprises a bioactive coating for promoting fusion to anchor to bone tissue.

17. The system of claim 1, wherein the main body further comprises screw holes for direct fixation to bone with fixation screws.

18. The system of claim 1, further comprising at least one trial device configured to determine a morphological profile of an implantation site.

19. The system of claim 1, further comprising an inserter tool having an arm configured to engage the main body.

* * * * *